(12) United States Patent
Wogulis

(10) Patent No.: US 8,828,701 B2
(45) Date of Patent: Sep. 9, 2014

(54) CELLOBIOHYDROLASE VARIANTS AND POLYNUCLEOTIDES ENCODING SAME

(75) Inventor: Mark Wogulis, Davis, CA (US)

(73) Assignee: Novozymes, Inc., Davis, CA (US)

(*) Notice: Subject to any disclaimer, the term of this patent is extended or adjusted under 35 U.S.C. 154(b) by 0 days.

(21) Appl. No.: 13/636,994

(22) PCT Filed: Mar. 29, 2011

(86) PCT No.: PCT/US2011/030352
§ 371 (c)(1),
(2), (4) Date: Sep. 24, 2012

(87) PCT Pub. No.: WO2011/123450
PCT Pub. Date: Oct. 6, 2011

(65) Prior Publication Data
US 2013/0040346 A1 Feb. 14, 2013

Related U.S. Application Data

(60) Provisional application No. 61/319,672, filed on Mar. 31, 2010.

(51) Int. Cl.
*C12N 9/42* (2006.01)
*C12N 9/14* (2006.01)
*C12P 19/14* (2006.01)
*C12P 7/14* (2006.01)
*C12P 19/34* (2006.01)
*C12P 21/06* (2006.01)
*C12N 15/00* (2006.01)
*C07H 21/04* (2006.01)
*C07K 1/00* (2006.01)

(52) U.S. Cl.
CPC .............. *C12N 9/2437* (2013.01); *C12P 19/14* (2013.01); *C12Y 302/01091* (2013.01)
USPC ............. 435/209; 435/195; 435/99; 435/162; 435/69.1; 435/91.1; 435/320.1; 435/252.3; 435/254.11; 536/23.1; 536/23.2; 530/350

(58) Field of Classification Search
USPC ................. 435/209, 195, 99, 162, 69.1, 91.1, 435/320.1, 252.3, 254.11; 536/23.1, 23.2; 530/350
See application file for complete search history.

(56) References Cited

U.S. PATENT DOCUMENTS 8,101,393 B2 * 1/2012 Gray et al. .............. 435/209
8,124,394 B2 * 2/2012 Maiyuran et al. ........... 435/201

FOREIGN PATENT DOCUMENTS

| WO | 03012071 A2 | 2/2003 |
| WO | 2006074005 A2 | 7/2006 |
| WO | 2008095033 A2 | 8/2008 |
| WO | 2010141779 A1 | 12/2010 |
| WO | 2011050037 A1 | 4/2011 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Fedorova et al., Genomic islands in the pathigenic filamentous fungus *Aspergillus fumigatus*. PLoS Genetics, 2008, vol. 4(4): e1000046, total 13 pages.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Fedorcova et al, 2010, UniProt Access No. B0XWL3.
Heinzelman et al, 2009, J Biol Chem 284, 26229-26233.
Heinzelman et al, 2009, Proc Natl Acad Sci USA 106, 5610-5615.
Liu et al, 2005, UniProt Access No. Q5G2D4.
Nierman et al, 2010, UniProt Access No. Q4WFK4.
Wen et al, 2009, Curr Op Biotechnol 20(4), 412-419.

* cited by examiner

*Primary Examiner* — Ganapathirama Raghu
(74) *Attorney, Agent, or Firm* — Robert L. Stames

(57) ABSTRACT

The present invention relates to variants of a parent cellobiohydrolase. The present invention also relates to polynucleotides encoding the cellobiohydrolase variants; nucleic acid constructs, vectors, and host cells comprising the polynucleotides; and methods of using the cellobiohydrolase variants.

23 Claims, 3 Drawing Sheets

US 8,828,701 B2

CELLOBIOHYDROLASE VARIANTS AND POLYNUCLEOTIDES ENCODING SAME

CROSS-REFERENCE TO RELATED APPLICATIONS

This application is a 35 U.S.C. 371 national application of PCT/US2011/030352, filed on Mar. 29, 2011, which claims priority from U.S. provisional application Ser. No. 61/319,672, filed on Mar. 31, 2010. The contents of these applications are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form, which is incorporated herein by reference.

BACKGROUND OF THE INVENTION

1. Field of the Invention

The present invention relates to variants of a cellobiohydrolase, polynucleotides encoding the variants, methods of producing the variants, and methods of using the variants.

2. Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars are easily fermented by yeast into ethanol.

WO 2006/074005 discloses variants of a *Hypocrea jecorina* cellobiohydrolase II. Heinzelman et al., 2009, *Proceedings of the National Academy of Sciences USA* 106: 5610-5615 discloses a family of thermostable fungal cellulases created by structure-guided recombination. Heinzelman et al., 2009, *Journal of Biological Chemistry* 284: 26229-26233 discloses a single mutation that contributes to stability of a fungal cellulase.

It would be advantageous in the art to improve the ability of polypeptides having cellobiohydrolase activity to enhance enzymatic degradation of lignocellulosic feedstocks.

The present invention provides variants of a parent cellobiohydrolase with improved properties compared to its parent.

SUMMARY OF THE INVENTION

The present invention relates to isolated variants of a parent cellobiohydrolase, comprising a substitution at one or more (several) positions corresponding to positions 254, 285, 286, 330, 342 and 360 of SEQ ID NO: 2, wherein the variants have cellobiohydrolase activity. In one aspect, the isolated variants further comprise a substitution at one or more (several) positions corresponding to positions 245, 382, 420, 437, and 440 of SEQ ID NO: 2.

The present invention also relates to isolated polynucleotides encoding the variants; nucleic acid constructs, vectors, and host cells comprising the polynucleotides; and methods of producing the variants.

The present invention also relates to plants comprising an isolated polynucleotide encoding such a variant having cellobiohydrolase activity.

The present invention also relates to methods of producing such a variant having cellobiohydrolase activity, comprising: (a) cultivating a transgenic plant or a plant cell comprising a polynucleotide encoding the variant having cellobiohydrolase activity under conditions conducive for production of the variant; and (b) recovering the variant.

The present invention also relates to methods for degrading or converting a cellulosic material, comprising: treating the cellulosic material with an enzyme composition in the presence of such a variant having cellobiohydrolase activity. In one aspect, the method further comprises recovering the degraded or converted cellulosic material.

The present invention also relates to methods of producing a fermentation product, comprising: (a) saccharifying a cellulosic material with an enzyme composition in the presence of such a variant having cellobiohydrolase activity; (b) fermenting the saccharified cellulosic material of step (a) with one or more fermenting microorganisms to produce the fermentation product; and (c) recovering the fermentation product from the fermentation.

The present invention also relates to methods of fermenting a cellulosic material, comprising: fermenting the cellulosic material with one or more fermenting microorganisms, wherein the cellulosic material is saccharified with an enzyme composition in the presence of such a variant having cellobiohydrolase activity.

DETAILED DESCRIPTION OF THE INVENTION

Figure 1A:
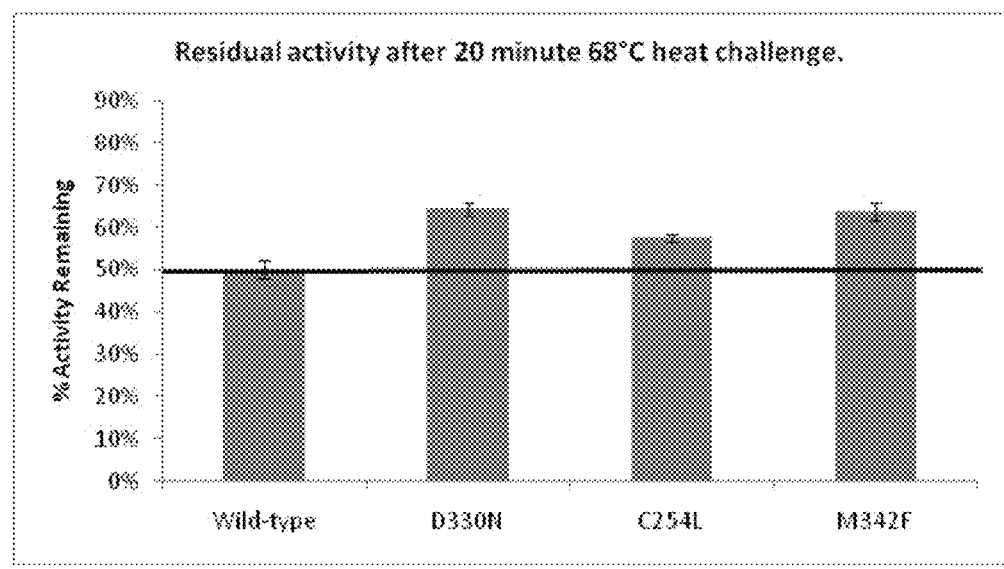
FIG. 1A shows a comparison of the residual activity for wild-type *Aspergillus fumigatus* family GH6A cellobiohydrolase and several individual variants of the *Aspergillus fumigatus* family GH6A cellobiohydrolase.

The present invention relates to isolated variants of a parent cellobiohydrolase, comprising a substitution at one or more (several) positions corresponding to positions 254, 285, 286, 330, 342, and 360 of SEQ ID NO: 2, wherein the variants have cellobiohydrolase activity. In some aspects, the variants have improved thermostability.

DEFINITIONS

Cellobiohydrolase: The term "cellobiohydrolase" means a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). For purposes of the present invention, cellobiohydrolase activity is determined using a fluorescent disaccharide derivative 4-methylumbelliferyl-β-D-lactoside according to the procedures described by van Tilbeurgh et al., 1982, *FEBS Letters* 149: 152-156 and van Tilbeurgh and Claeyssens, 1985, *FEBS Letters* 187: 283-288. "Cellobiohydrolase activity" means hydrolytic activity of cellulosic material catalyzed by a cellobiohydrolase.

Cellulolytic activity: The term "cellulolytic activity" means a biological activity that hydrolyzes a cellulosic material. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No. 1 filter paper, microcrystalline cellulose, bacterial cellulose, algal cellulose, cotton, pretreated lignocellulose, etc. The most common total cellulolytic activity assay is the filter paper assay using Whatman No. 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic activity is determined by measuring the increase in hydrolysis of a cellulosic material by cellulolytic enzyme(s) under the following conditions: 1-20 mg of cellulolytic protein/g of cellulose in PCS for 3-7 days at 50-65° C. compared to a control hydrolysis without addition of cellulolytic protein. Typical conditions are 1 ml reactions, washed or unwashed PCS, 5% insoluble solids, 50 mM sodium acetate pH 5, 1 mM $MnSO_4$, 50-65° C., 72 hours, sugar analysis by AMINEX® HPX-87H column (Bio-Rad Laboratories, Inc., Hercules, Calif., USA).

Endoglucanase: The term "endoglucanase" means an endo-1,4-(1,3;1,4)-beta-D-glucan 4-glucanohydrolase (E.C. 3.2.1.4), which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268.

Beta-glucosidase: The term "beta-glucosidase" means a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenol produced per minute at 40° C., pH 5 from 1 mM p-nitrophenyl-beta-D-glucopyranoside as substrate in 100 mM sodium citrate containing 0.01% TWEEN® 20.

Cellulolytic enhancing activity: The term "cellulolytic enhancing activity" means a biological activity catalyzed by GH61 polypeptide that enhances the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic protein and 0.5-50% w/w protein of a GH61 polypeptide having cellulolytic enhancing activity for 1-7 day at 50-65° C. compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsværd, Denmark) in the presence of 3% of total protein weight *Aspergillus oryzae* beta-glucosidase (recombinantly produced in *Aspergillus oryzae* according to WO 02/095014) or 3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the cellulolytic enhancing activity of the mature polypeptide of a GH61 polypeptide.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, more preferably at least 1.05-fold, more preferably at least 1.10-fold, more preferably at least 1.25-fold, more preferably at least 1.5-fold, more preferably at least 2-fold, more preferably at least 3-fold, more preferably at least 4-fold, more preferably at least 5-fold, even more preferably at least 10-fold, and most preferably at least 20-fold.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Family 6 glycoside hydrolase: The term "Family 6 glycoside hydrolase" or "Family GH6" or "GH6" means a polypeptide falling into the glycoside hydrolase Family 6 according to Henrissat B., 1991, supra, and Henrissat B., and Bairoch A., 1996, supra.

Xylan degrading activity: The terms "xylan degrading activity" or "xylanolytic activity" mean a biological activity that hydrolyzes xylan-containing material. The two basic approaches for measuring xylanolytic activity include: (1) measuring the total xylanolytic activity, and (2) measuring the individual xylanolytic activities (endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endo-hydrolysis of 1,4-beta-D-xylosidic linkages in xylans. For purposes of the present invention, xylanase activity is determined using birchwood xylan as substrate. One unit of xylanase is defined as 1.0 mmole of reducing sugar (measured in glucose equivalents as described by Lever, 1972, A new reaction for colorimetric determination of carbohydrates, *Anal. Biochem* 47: 273-279) produced per minute during the initial period of hydrolysis at 50° C., pH 5 from 2 g of birchwood xylan per liter as substrate in 50 mM sodium acetate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides, to remove successive D-xylose residues from the non-reducing termini. For purposes of the present invention, one unit of beta-xylosidase is defined as 1.0 µmole of p-nitrophenol produced per minute at 40° C., pH 5 from 1 mM p-nitrophenyl-beta-D-xyloside as substrate in 100 mM sodium citrate containing 0.01% TWEEN® 20.

Acetylxylan esterase: The term "acetylxylan esterase" means a carboxylesterase (EC 3.1.1.72) that catalyses the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20. One unit of acetylxylan esterase is defined as the amount of enzyme capable of releasing 1 µmole of p-nitrophenolate anion per minute at pH 5, 25° C.

Feruloyl esterase: The term "feruloyl esterase" means a 4-hydroxy-3-methoxycinnamoyl-sugar hydrolase (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 µmole of p-nitrophenolate anion per minute at pH 5, 25° C.

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 µmole of glucuronic or 4-O-methyl-glucuronic acid per minute at pH 5, 40° C.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, Calif., USA).

Cellulosic material: The cellulosic material can be any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is lignocellulose.

In one aspect, the cellulosic material is herbaceous material. In another aspect, the cellulosic material is agricultural residue. In another aspect, the cellulosic material is forestry residue. In another aspect, the cellulosic material is municipal solid waste. In another aspect, the cellulosic material is waste paper. In another aspect, the cellulosic material is pulp and paper mill residue.

In another aspect, the cellulosic material is corn stover. In another aspect, the cellulosic material is corn fiber. In another aspect, the cellulosic material is corn cob. In another aspect, the cellulosic material is orange peel. In another aspect, the cellulosic material is rice straw. In another aspect, the cellulosic material is wheat straw. In another aspect, the cellulosic material is switch grass. In another aspect, the cellulosic material is miscanthus. In another aspect, the cellulosic material is bagasse.

In another aspect, the cellulosic material is microcrystalline cellulose. In another aspect, the cellulosic material is bacterial cellulose. In another aspect, the cellulosic material is algal cellulose. In another aspect, the cellulosic material is cotton linter. In another aspect, the cellulosic material is amorphous phosphoric-acid treated cellulose. In another aspect, the cellulosic material is filter paper.

The cellulosic material may be used as is or may be subjected to pretreatment, using conventional methods known in the art, as described herein. In a preferred aspect, the cellulosic material is pretreated.

Pretreated corn stover: The term "PCS" or "Pretreated Corn Stover" means a cellulosic material derived from corn stover by treatment with heat and dilute sulfuric acid.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the methods of the present invention, any material containing xylan may be used. In a preferred aspect, the xylan-containing material is lignocellulose.

Variant: The term "variant" means a polypeptide having cellobiohydrolase activity comprising an alteration, i.e., a substitution, insertion, and/or deletion, at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

Mutant: The term "mutant" means a polynucleotide encoding a variant.

Wild-Type: The term "wild-type" (e.g., as used in wild-type protein, wild-type polypeptide, or wild-type cellobiohydrolase) describes the indicated polypeptide which as been expressed by a naturally occurring microorganism, such as a bacterium, yeast, or filamentous fungus found in nature.

Parent or parent cellobiohydrolase: The term "parent" or "parent cellobiohydrolase" means a cellobiohydrolase to which an alteration is made to produce a cellobiohydrolase variant of the present invention. The parent may be a naturally occurring (wild-type) polypeptide or a variant thereof. For instance, the parent polypeptide may be a variant of a wild-type polypeptide. A parent may also be an allelic variant, which is a polypeptide encoded by any of two or more alternative forms of a gene occupying the same chromosomal locus.

Isolated: The terms "isolated" and "purified" mean a polypeptide or polynucleotide that is removed from at least one component with which it is naturally associated. For example, a variant or polypeptide may be at least 1% pure, e.g., at least 5% pure, at least 10% pure, at least 20% pure, at least 40% pure, at least 60% pure, at least 80% pure, at least 90% pure, and at least 95% pure, as determined by SDS-PAGE and a polynucleotide may be at least 1% pure, e.g., at least 5% pure, at least 10% pure, at least 20% pure, at least 40% pure, at least 60% pure, at least 80% pure, at least 90% pure, and at least 95% pure, as determined by agarose electrophoresis.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 20 to 454 of SEQ ID NO: 2 based on the Sigcleave program (von Heijne G., 1986, *Nucleic Acids Res.* 14: 4683-4690) that predicts amino acids 1 to 19 of SEQ ID NO: 2 are a signal peptide.

Mature polypeptide coding sequence: The term "mature polypeptide coding sequence" means a polynucleotide that encodes a mature polypeptide having cellobiohydrolase activity (e.g., cDNA or genomic DNA). In one aspect, the mature polypeptide coding sequence is nucleotides 58 to 1710 of SEQ ID NO: 1 based on the Sigcleave program (von Heijne G., 1986, supra) that predicts nucleotides 1 to 57 of SEQ ID NO: 1 encode a signal peptide. In another aspect, the mature polypeptide coding sequence is the cDNA sequence contained in nucleotides 58 to 1710 of SEQ ID NO: 1.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (ob tained using the -nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Fragment: The term "fragment" means a polypeptide having one or more (several) amino acids deleted from the amino and/or carboxyl terminus of a mature polypeptide; wherein the fragment has cellobiohydrolase activity. In one aspect, a fragment contains at least 370 amino acid residues, at least 390 amino acid residues, and at least 410 amino acid residues.

Subsequence: The term "subsequence" means a polynucleotide having one or more (several) nucleotides deleted from the 5'- and/or 3'-end of a mature polypeptide coding sequence; wherein the subsequence encodes a fragment having cellobiohydrolase activity. In one aspect, a subsequence contains at least 1110 nucleotides, at least 1170 nucleotides, and at least 1230 nucleotides.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Coding sequence: The term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" means all components necessary for the expression of a polynucleotide encoding a variant of the present invention. Each control sequence may be native or foreign to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to, thermal activity, thermostability, pH activity, pH stability, substrate/cofactor specificity, improved surface properties, product specificity, increased stability or solubility in the presence of pretreated biomass, improved stability under storage conditions, and chemical stability.

Improved thermostability: The term "improved thermostability" means a variant displaying retention of cellobiohydrolase activity after a period of incubation at elevated temperature relative to the parent, either in a buffer or under conditions such as those which exist during product storage/transport or conditions similar to those that exist during industrial use of the variant. A variant may or may not display an altered thermal activity profile relative to the parent. For example, a variant may have an improved ability to refold following incubation at an elevated temperature relative to the parent.

In one aspect, the thermostability of the variant having cellobiohydrolase activity is at least 1.05-fold, e.g., at least 1.1-fold, at least 1.5-fold, at least 1.8-fold, at least 2-fold, at least 5-fold, at least 10-fold, at least 15-fold, at least 20-fold, and at least 25-fold more thermostable than the parent when residual activity following a 20 minute heat challenge at 67° C. in 100 mM NaCl-50 mM sodium acetate pH 5.0 buffer is compared using a biomass hydrolysis assay, in which an equivalent addition of either the variant having cellobiohydrolase activity or parent enzyme, expressed in mg protein per gram cellulose, is added to PASC at a fixed temperature of 50° C. at pH 5 for a total hydrolysis time of 30 minutes, at which point biomass hydrolysis is measured.

Conventions for Designation of Variants

For purposes of the present invention, the polypeptide disclosed in SEQ ID NO: 2 is used to determine the corresponding amino acid residue in another cellobiohydrolase. The amino acid sequence of another cellobiohydrolase is aligned with the polypeptide disclosed in SEQ ID NO: 2, and based on the alignment, the amino acid position number corresponding to any amino acid residue in the polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later.

Identification of the corresponding amino acid residue in another cellobiohydrolase can be confirmed by an alignment of multiple polypeptide sequences using "ClustalW" (Larkin et al., 2007, *Bioinformatics* 23: 2947-2948).

When the other enzyme has diverged from the polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementations of these algorithms can additionally be utilized to query structure databases with a structure of interest in order to discover possible structural homologs (e.g., Holm and Park, 2000, *Bioinformatics* 16: 566-567).

In describing the cellobiohydrolase variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine with alanine at position 226 is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position*. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G - K - A |

Multiple alterations. Variants comprising multiple alterations are separated by addition marks ("+"), e.g., "Arg170Tyr+Gly195Glu" or "R170Y+G195E" representing a substitution of tyrosine and glutamic acid for arginine and glycine at positions 170 and 195, respectively.

Different alterations. Where different alterations can be introduced at a position, the different alterations are separated by a comma, e.g., "Arg170Tyr,Glu" represents a substitution of arginine with tyrosine or glutamic acid at position 170. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

Parent Cellobiohydrolases

The parent cellobiohydrolase may be (a) a polypeptide having at least 60% sequence identity to the mature polypeptide of SEQ ID NO: 2; (b) a polypeptide encoded by a polynucleotide that hybridizes under low stringency conditions with (i) the mature polypeptide coding sequence of SEQ ID NO: 1, (ii) the cDNA sequence contained in the mature polypeptide coding sequence of SEQ ID NO: 1, or (iii) the full-length complementary strand of (i) or (ii); or (c) a polypeptide encoded by a polynucleotide having at least 60% sequence identity to the mature polypeptide coding sequence of SEQ ID NO: 1.

In a first aspect, the parent has a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have cellobiohydrolase activity. In one aspect, the amino acid sequence of the parent differs by no more than ten amino acids, e.g., by no more than five amino acids, four amino acids, three amino acids, two amino acids, or one amino acid from the mature polypeptide of SEQ ID NO: 2.

In one aspect, the parent comprises or consists of the amino acid sequence of SEQ ID NO: 2. In another aspect, the parent comprises or consists of the mature polypeptide of SEQ ID NO: 2. In another aspect, the parent comprises or consists of amino acids 20 to 454 of SEQ ID NO: 2.

In an embodiment, the parent is a fragment of the mature polypeptide of SEQ ID NO: 2 containing at least 370 amino acid residues, e.g., at least 390 and at least 410 amino acid residues.

In another embodiment, the parent is an allelic variant of the mature polypeptide of SEQ ID NO: 2.

In a second aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, (ii) the cDNA sequence contained in the mature polypeptide coding sequence of SEQ ID NO: 1, or (iii) the full-length complementary strand of (i) or (ii) (J. Sambrook, E. F. Fritsch, and T. Maniatis, 1989, *Molecular Cloning, A Laboratory Manual*, 2d edition, Cold Spring Harbor, N.Y.).

The polynucleotide of SEQ ID NO: 1 or a subsequence thereof, as well as the amino acid sequence of SEQ ID NO: 2 or a fragment thereof, may be used to design nucleic acid probes to identify and clone DNA encoding a parent from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may be screened for DNA that hybridizes with the probes described above and encodes a parent. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleotide probe corresponding to the polynucleotide shown in SEQ ID NO: 1, its full-length complementary strand, or a subsequence thereof, under low to very high stringency conditions. Molecules to which the probe hybridizes can be detected using, for example, X-ray film or any other detection means known in the art.

In one aspect, the nucleic acid probe is the mature polypeptide coding sequence of SEQ ID NO: 1. In another aspect, the nucleic acid probe is nucleotides 58 to 1710 of SEQ ID NO: 1. In another aspect, the nucleic acid probe is a polynucleotide that encodes the polypeptide of SEQ ID NO: 2 or a fragment thereof. In another aspect, the nucleic acid probe is SEQ ID NO: 1.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), 50° C. (low stringency), 55° C. (medium stringency), 60° C. (medium-high stringency), 65° C. (high stringency), or 70° C. (very high stringency).

For short probes that are about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48: 1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

In a third aspect, the parent is encoded by a polynucleotide having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which encodes a polypeptide having cellobiohydrolase activity. In one aspect, the mature polypeptide coding sequence is nucleotides 58 to 1710 of SEQ ID NO: 1. In an embodiment, the parent is encoded by a polynucleotide comprising or consisting of SEQ ID NO: 1.

The parent may be obtained from microorganisms of any genus. For purposes of the present invention, the term "obtained from" as used herein in connection with a given source shall mean that the parent encoded by a polynucleotide is produced by the source or by a cell in which the polynucleotide from the source has been inserted. In one aspect, the parent is secreted extracellularly.

The parent may be a bacterial cellobiohydrolase. For example, the parent may be a gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* cellobiohydrolase, or a gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* cellobiohydrolase.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* cellobiohydrolase.

In another aspect, the parent is a *Streptococcus equisimilis, Streptococcus pyogenes, Streptococcus uberis*, or *Streptococcus equi* subsp. *Zooepidemicus* cellobiohydrolase.

In another aspect, the parent is a *Streptomyces achromogenes, Streptomyces avermitilis, Streptomyces coelicolor, Streptomyces griseus,* or *Streptomyces lividans* cellobiohydrolase.

The parent may be a fungal cellobiohydrolase. For example, the parent may be a yeast cellobiohydrolase such as a *Candida, Kluyveromyces, Pichia, Saccharomyces, Schizosaccharomyces,* or *Yarrowia* cellobiohydrolase. For example, the parent may be a filamentous fungal cellobiohydrolase such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* cellobiohydrolase.

In another aspect, the parent is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* cellobiohydrolase.

In another aspect, the parent is an *Acremonium cellulolyticus, Aspergillus aculeatus, Aspergillus awamori, Aspergillus foetidus, Aspergillus Fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* cellobiohydrolase.

In another aspect, the parent is an *Aspergillus* cellobiohydrolase, such as an *Aspergillus fumigatus* cellobiohydrolase, e.g., the cellobiohydrolase of SEQ ID NO: 2 or the mature polypeptide thereof.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc,) using the above-mentioned probes. Techniques for isolating microorganisms and DNA directly from natural habitats are well known in the art. The polynucleotide encoding a parent may then be derived by similarly screening a genomic or cDNA library of another microorganism or mixed DNA sample. Once a polynucleotide encoding a parent has been detected with a probe(s), the polynucleotide may be isolated or cloned by utilizing techniques that are known to those of ordinary skill in the art (see, e.g., Sambrook et al., 1989, supra).

The parent may be a hybrid polypeptide in which a portion of one polypeptide is fused at the N-terminus or the C-terminus of a portion of another polypeptide.

The parent also may be a fused polypeptide or cleavable fusion polypeptide in which one polypeptide is fused at the N-terminus or the C-terminus of another polypeptide. A fused polypeptide is produced by fusing a polynucleotide encoding one polypeptide to a polynucleotide encoding another polypeptide. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Preparation of Variants

The present invention also relates to methods for obtaining a variant having cellobiohydrolase activity, comprising: (a) introducing into a parent cellobiohydrolase a substitution at one or more (several) positions corresponding to positions 254, 285, 286, 330, 342, and 360 of the mature polypeptide of SEQ ID NO: 2, wherein the variant has cellobiohydrolase activity; and (b) recovering the variant. In one aspect, the method further comprises introducing into the parent cellobiohydrolase a substitution at one or more (several) positions corresponding to positions 254, 285, 286, 330, 342, and 360 of SEQ ID NO: 2.

The variants can be prepared using any mutagenesis procedure known in the art, such as site-directed mutagenesis, synthetic gene construction, semi-synthetic gene construction, random mutagenesis, shuffling, etc.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156;

WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Site-directed mutagenesis is a technique in which one or more (several) mutations are created at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests at the plasmid and the oligonucleotide is the same, permitting sticky ends of the plasmid and insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotide are synthesized and assembled upon photo-programmable microfluidic chips.

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR implication. Polynucleotide subsequences may then be shuffled.

Variants

The present invention also provides variants of a parent cellobiohydrolase comprising a substitution at one or more (several) positions corresponding to positions 254, 285, 286, 330, 342, and 360 of SEQ ID NO: 2, wherein the variant has cellobiohydrolase activity.

In an aspect, the variant has sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent cellobiohydrolase.

In another aspect, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, and at least 99%, but less than 100%, sequence identity to the mature polypeptide of SEQ ID NO: 2.

In one aspect, the variants of the present invention comprise 1-5 substitutions, such as 1, 2, 3, 4, or 5 substitutions. In another aspect, the variants of the present invention comprise 1-3 substitutions, such as 1, 2, or 3 substitutions.

In one aspect, a variant comprises a substitution at one or more (several) positions corresponding to positions 254, 285, 286, 330, 342, and 360 of SEQ ID NO: 2. In another aspect, the variant comprises or consists of one or more (several) substitutions selected from C254L, L285I, G286Q, D330N, M342F, and S360G corresponding to SEQ ID NO: 2.

In one aspect, a variant comprises a substitution at any one position corresponding to positions 254, 285, 286, 330, 342, and 360 of SEQ ID NO: 2. In another aspect, the variant comprises or consists of one substitution selected from C254L, L285I, G286Q, D330N, M342F, and S360G corresponding to SEQ ID NO: 2.

In one aspect, the variant comprises or consists of a substitution at a position corresponding to position 254 of SEQ ID NO: 2. In another aspect, the amino acid at a position corresponding to position 254 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant comprises or consists of the substitution C254L corresponding to SEQ ID NO: 2.

In one aspect, the variant comprises or consists of a substitution at a position corresponding to position 285 of SEQ ID NO: 2. In another aspect, the amino acid at a position corresponding to position 285 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the variant comprises or consists of the substitution L285I corresponding to SEQ ID NO: 2.

In one aspect, the variant comprises or consists of a substitution at a position corresponding to position 286 of SEQ ID NO: 2. In another aspect, the amino acid at a position corresponding to position 286 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln. In another aspect, the variant comprises or consists of the substitution G286Q corresponding to SEQ ID NO: 2.

In one aspect, the variant comprises or consists of a substitution at a position corresponding to position 286 of SEQ ID NO: 2 together with a substitution at a position corresponding to position 286 of SEQ ID NO: 2. In another aspect, the amino acids at the positions corresponding to positions 285 and 286 are substituted with Ala, Arg, Asn, Asp, Cys, Gln, Glu, Gly, His, Ile, Leu, Lys, Met, Phe, Pro, Ser, Thr, Trp, Tyr, or Val, preferably with Ile and Gln, for positions 285 and 286, respectively. In another aspect, the variant comprises or consists of the substitution L285I together with the substitution G286Q corresponding to SEQ ID NO: 2.

In another aspect, the variant comprises or consists of a substitution at a position corresponding to position 330 of SEQ ID NO: 2. In another aspect, the amino acid at a position corresponding to position 330 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn. In another aspect, the variant comprises or consists of the substitution D330N corresponding to SEQ ID NO: 2.

In another aspect, the variant comprises or consists of a substitution at a position corresponding to position 342 of SEQ ID NO: 2. In another aspect, the amino acid at a position corresponding to position 342 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe. In another aspect, the variant comprises or consists of the substitution M342F corresponding to SEQ ID NO: 2.

In another aspect, the variant comprises or consists of a substitution at a position corresponding to position 360 of SEQ ID NO: 2. In another aspect, the amino acid at a position corresponding to position 360 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gly. In another aspect, the variant comprises or consists of the substitution S360G corresponding to SEQ ID NO: 2.

In one aspect, the variant comprises or consists of substitutions at any two positions corresponding to positions 254, 285, 286, 330, 342, and 360 of SEQ ID NO: 2 (e.g., 285 and 286), such as those described above. In one aspect, the variant comprises or consists of substitutions at positions corresponding to positions 254 and 285 of SEQ ID NO: 2, such as those described above. In another aspect, the variant comprises or consists of substitutions at positions corresponding to positions 254 and 286, such as those described above. In another aspect, the variant comprises or consists of substitutions at positions corresponding to positions 254 and 330, such as those described above. In another aspect, the variant comprises or consists of substitutions at positions corresponding to positions 254 and 342, such as those described above. In another aspect, the variant comprises or consists of substitutions at positions corresponding to positions 254 and 360, such as those described above. In another aspect, the variant comprises or consists of substitutions at positions corresponding to positions 285 and 286, such as those described above. In another aspect, the variant comprises or consists of substitutions at positions corresponding to positions 285 and 330, such as those described above. In another aspect, the variant comprises or consists of substitutions at positions corresponding to positions 285 and 342, such as those described above. In another aspect, the variant comprises or consists of substitutions at positions corresponding to positions 285 and 360, such as those described above. In another aspect, the variant comprises or consists of substitutions at positions corresponding to positions 286 and 330, such as those described above. In another aspect, the variant comprises or consists of substitutions at positions corresponding to positions 286 and 342, such as those described above. In another aspect, the variant comprises or consists of substitutions at positions corresponding to positions 286 and 360, such as those described above.

In one aspect, the variant comprises or consists of two substitutions selected from C254L, L285I, G286Q, D330N, M342F, and S360G corresponding to SEQ ID NO: 2. In one aspect, the variant comprises or consists of substitutions C254L+L285I. In another aspect, the variant comprises or consists of substitutions C254L+G286Q. In another aspect, the variant comprises or consists of substitutions C254L+D330N. In another aspect, the variant comprises or consists of substitutions C254L+M342F. In another aspect, the variant comprises or consists of substitutions C254L+S360G. In another aspect, the variant comprises or consists of substitutions L285I+G286Q. In another aspect, the variant comprises or consists of substitutions L285I+D330N. In another aspect, the variant comprises or consists of substitutions L285I+M342F. In another aspect, the variant comprises or consists of substitutions L285I+S360G. In another aspect, the variant comprises or consists of substitutions G286Q+D330N. In another aspect, the variant comprises or consists of substitutions G286Q+M342F. In another aspect, the variant comprises or consists of substitutions G286Q+S360G.

In one aspect, the variant comprises or consists of substitutions at any three positions corresponding to positions 254, 285, 286, 330, 342, and 360 of SEQ ID NO: 2, such as those described above. In one aspect, the variant comprises or consists of substitutions at positions corresponding to positions 254, 285, and 286 of SEQ ID NO: 2, such as those described above. In another aspect, the variant comprises or consists of substitutions at positions corresponding to positions 254, 285, and 330, such as those described above. In another aspect, the variant comprises or consists of substitutions at positions corresponding to positions 254, 285, and 342, such as those described above. In another aspect, the variant comprises or consists of substitutions at positions corresponding to positions 254, 285, and 360, such as those described above. In another aspect, the variant comprises or consists of substitutions at positions corresponding to positions 254, 286, and 330, such as those described above. In another aspect, the variant comprises or consists of substitutions at positions corresponding to positions 254, 286, and 342, such as those described above. In another aspect, the variant comprises or consists of substitutions at positions corresponding to positions 254, 286, and 360, such as those described above. In another aspect, the variant comprises or consists of substitutions at positions corresponding to positions 254, 330, and 342, such as those described above. In another aspect, the variant comprises or consists of substitutions at positions corresponding to positions 254, 330, and 360, such as those described above. In another aspect, the variant comprises or consists of substitutions at positions corresponding to positions 254, 342, and 360, such as those described above. In another aspect, the variant comprises or consists of substitutions at positions corresponding to positions 285, 286, and 330, such as those described above. In another aspect, the variant comprises or consists of substitutions at positions corresponding to positions 285, 286, and 342, such as those described above. In another aspect, the variant comprises or consists of substitutions at positions corresponding to positions 285, 286, and 360, such as those described above. In another aspect, the variant comprises or consists of substitutions at positions corresponding to positions 285, 330, and 342, such as those described above. In another aspect, the variant comprises or consists of substitutions at positions corresponding to positions 285, 330, and 360, such as those described above. In another aspect, the variant comprises or consists of substitutions at positions corresponding to positions 285, 342, and 360, such as those described above. In another aspect, the variant comprises or consists of substitutions at positions corresponding to positions 286, 330, and 342, such as those described above. In another aspect, the variant comprises or consists of substitutions at positions corresponding to positions 286, 330, and 360, such as those described above. In another aspect, the variant comprises or consists of substitutions at positions corresponding to positions 286, 342, and 360, such as those described above. In another aspect, the variant comprises or consists of substitutions at positions corresponding to positions 330, 342, and 360, such as those described above.

In another aspect, the variant comprises or consists of three substitutions selected from C254L, L285I, G286Q, D330N, M342F, and S360G corresponding to SEQ ID NO: 2. In one aspect, the variant comprises or consists of the substitutions C254L+L285I+G286Q. In another aspect, the variant comprises or consists of the substitutions C254L+L285I+D330N. In another aspect, the variant comprises or consists of the substitutions C254L+L285I+M342F. In another aspect, the variant comprises or consists of the substitutions C254L+L285I+S360G. In another aspect, the variant comprises or consists of the substitutions C254L+G286Q+D330N. In another aspect, the variant comprises or consists of the substitutions C254L+G286Q+M342F. In another aspect, the variant comprises or consists of the substitutions C254L+G286Q+S360G. In another aspect, the variant comprises or consists of the substitutions C254L+D330N+M342F. In another aspect, the variant comprises or consists of the substitutions C254L+D330N+S360G. In another aspect, the variant comprises or consists of the substitutions C254L+M342F+S360G. In another aspect, the variant comprises or consists of the substitutions L285I+G286Q+D330N. In another aspect, the variant comprises or consists of the substitutions L285I+G286Q+M342F. In another aspect, the variant comprises or consists of the substitutions L285I+G286Q+S360G. In another aspect, the variant comprises or consists of the substitutions L285I+D330N+M342F. In another aspect, the variant comprises or consists of the substitutions L285I+D330N+S360G. In another aspect, the variant comprises or consists of the substitutions L285I+M342F+S360G. In another aspect, the variant comprises or consists of the substitutions G286Q+D330N+M342F. In another aspect, the variant comprises or consists of the substitutions G286Q+D330N+S360G. In another aspect, the variant comprises or consists of the substitutions G286Q+M342F+S360G. In another aspect, the variant comprises or consists of the substitutions D330N+M342F+S360G.

In one aspect, the variant comprises or consists of substitutions at any four positions corresponding to positions 254, 285, 286, 330, 342, and 360 of SEQ ID NO: 2, such as those described above. In one aspect, the variant comprises or consists of substitutions at positions corresponding to positions 254, 285, 286, and 330 of SEQ ID NO: 2, such as those described above. In another aspect, the variant comprises or consists of substitutions at positions corresponding to positions 254, 285, 286, and 342, such as those described above. In another aspect, the variant comprises or consists of substitutions at positions corresponding to positions 254, 285, 330, and 342, such as those described above. In another aspect, the variant comprises or consists of substitutions at positions corresponding to positions 254, 286, 330, and 342, such as those described above. In another aspect, the variant comprises or consists of substitutions at positions corresponding to positions 285, 286, 330, and 342, such as those described above. In another aspect, the variant comprises or consists of substitutions at positions corresponding to positions 254, 285, 286, and 360, such as those described above. In another aspect, the variant comprises or consists of substitutions at positions corresponding to positions 254, 285, 330, and 360, such as those described above. In another aspect, the variant comprises or consists of substitutions at positions corresponding to positions 254, 286, 330, and 360, such as those described above. In another aspect, the variant comprises or consists of substitutions at positions corresponding to positions 285, 286, 330, and 360, such as those described above. In another aspect, the variant comprises or consists of substitutions at positions corresponding to positions 254, 285, 342, and 360, such as those described above. In another aspect, the variant comprises or consists of substitutions at positions corresponding to positions 254, 286, 342, and 360, such as those described above. In another aspect, the variant comprises or consists of substitutions at positions corresponding to positions 285, 286, 342, and 360, such as those described above. In another aspect, the variant comprises or consists of substitutions at positions corresponding to positions 254, 330, 342, and 360, such as those described above. In another aspect, the variant comprises or consists of substitutions at positions corresponding to positions 285, 330, 342, and 360, such as those described above. In another aspect, the variant comprises or consists of substitutions at positions corresponding to positions 286, 330, 342, and 360, such as those described above.

In another aspect, the variant comprises or consists of four substitutions selected from C254L, L285I, G286Q, D330N, M342F, and S360G corresponding to SEQ ID NO: 2. In one aspect, the variant comprises or consists of the substitutions C254L+L285I+G286Q+D330N. In another aspect, the variant comprises or consists of the substitutions C254L+L285I+G286Q+M342F. In another aspect, the variant comprises or consists of the substitutions C254L+L285I+D330N+M342F. In another aspect, the variant comprises or consists of the substitutions C254L+G286Q+D330N+M342F. In another aspect, the variant comprises or consists of the substitutions L285I+G286Q+D330N+M342F. In another aspect, the variant comprises or consists of the substitutions C254L+L285I+G286Q+S360G. In another aspect, the variant comprises or consists of the substitutions C254L+L285I+D330N+S360G. In another aspect, the variant comprises or consists of the substitutions C254L+G286Q+D330N+S360G. In another aspect, the variant comprises or consists of the substitutions L285I+G286Q+D330N+S360G. In another aspect, the variant comprises or consists of the substitutions C254L+L285I+M342F+S360G. In another aspect, the variant comprises or consists of the substitutions C254L+G286Q+M342F+S360G. In another aspect, the variant comprises or consists of the substitutions L285I+G286Q+M342F+S360G. In another aspect, the variant comprises or consists of the substitutions C254L+D330N+M342F+S360G. In another aspect, the variant comprises or consists of the substitutions L285I+D330N+M342F+S360G. In another aspect, the variant comprises or consists of the substitutions G286Q+D330N+M342F+S360G.

In one aspect, the variant comprises or consists of substitutions at any five positions corresponding to positions 254, 285, 286, 330, 342, and 360 of SEQ ID NO: 2, such as those described above. In one aspect, the variant comprises or consists of substitutions at positions corresponding to positions 285, 286, 330, 342, and 360 of SEQ ID NO: 2, such as those described above. In another aspect, the variant comprises or consists of substitutions at positions corresponding to positions 254, 286, 330, 342, and 360, such as those described above. In another aspect, the variant comprises or consists of substitutions at positions corresponding to positions 254, 285, 330, 342, and 360, such as those described above. In another aspect, the variant comprises or consists of substitutions at positions corresponding to positions 254, 285, 286, 342, and 360, such as those described above. In another aspect, the variant comprises or consists of substitutions at positions corresponding to positions 254, 285, 286, 330, and 360, such as those described above. In another aspect, the variant comprises or consists of substitutions at positions corresponding to positions 254, 285, 286, 330, and 342, such as those described above.

In another aspect, the variant comprises or consists of five substitutions selected from C254L, L285I, G286Q, D330N, M342F, and S360G corresponding to SEQ ID NO: 2. In one aspect, the variant comprises or consists of the substitutions L285I+G286Q+D330N+M342F+S360G. In another aspect, the variant comprises or consists of the substitutions C254L+

G286Q+D330N+M342F+S360G. In another aspect, the variant comprises or consists of the substitutions C254L+L285I+D330N+M342F+S360G. In another aspect, the variant comprises or consists of the substitutions C254L+L285I+G286Q+M342F+S360G. In another aspect, the variant comprises or consists of the substitutions C254L+L285I+G286Q+D330N+S360G. In another aspect, the variant comprises or consists of the substitutions C254L+L285I+G286Q+D330N+M342F.

In another aspect, the variant comprises or consists of substitutions corresponding to positions 254, 285, 286, 330, 342, and 360 of SEQ ID NO: 2, such as those described above. In another aspect, the variant comprises or consists of the substitutions C254L+L285I+G286Q+D330N+M342F+S360G corresponding to SEQ ID NO: 2.

The variants may further comprise an alteration at one or more (several) other positions. In one aspect, the variants of the present invention comprise 1-5 further alterations, such as 1, 2, 3, 4, or 5 alterations. In another aspect, the variants of the present invention further comprise 1-5 substitutions, such as 1, 2, 3, 4, or 5 substitutions.

In one aspect, a variant comprises or consists of a substitution at one or more (several) positions corresponding to positions 245, 382, 420, 437, and 440 of SEQ ID NO: 2. In another aspect, the variant comprises or consists of one or more (several) substitutions selected from A245S, G382C, L420I, T437Q, and Q440C corresponding to SEQ ID NO: 2.

In one aspect, a variant comprises or consists of a substitution at any one position corresponding to positions 245, 382, 420, 437, and 440 of SEQ ID NO: 2. In another aspect, the variant comprises or consists of one substitution selected from A245S, G382C, L420I, T437Q, and Q440C corresponding to SEQ ID NO: 2.

In one aspect, the variant further comprises a substitution at a position corresponding to position 245 of SEQ ID NO: 2. In another aspect, the amino acid at a position corresponding to position 245 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser. In another aspect, the variant further comprises or consists of the substitution A245S corresponding to SEQ ID NO: 2.

In one aspect, the variant further comprises a substitution at a position corresponding to position 382 of SEQ ID NO: 2. In another aspect, the amino acid at a position corresponding to position 382 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys. In another aspect, the variant further comprises or consists of the substitution G382C corresponding to SEQ ID NO: 2.

In one aspect, the variant further comprises a substitution at a position corresponding to position 420 of SEQ ID NO: 2. In another aspect, the amino acid at a position corresponding to position 420 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the variant further comprises or consists of the substitution L420I corresponding to SEQ ID NO: 2.

In one aspect, the variant further comprises a substitution at a position corresponding to position 437 of SEQ ID NO: 2. In another aspect, the amino acid at a position corresponding to position 437 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln. In another aspect, the variant further comprises or consists of the substitution T437Q corresponding to SEQ ID NO: 2.

In one aspect, the variant further comprises a substitution at a position corresponding to position 440 of SEQ ID NO: 2. In another aspect, the amino acid at a position corresponding to position 440 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys. In another aspect, the variant further comprises or consists of the substitution Q440C corresponding to SEQ ID NO: 2. In one aspect, the variant further comprises or consists of the substitutions G382C and Q440C corresponding to SEQ ID NO: 2.

In one aspect, the variant further comprises or consists of substitutions at any two positions corresponding to positions 245, 382, 420, 437, and 440 of SEQ ID NO: 2, such as those described above. In one aspect, the variant further comprises or consists of a substitution at positions corresponding to positions 420 and 437 of SEQ ID NO: 2, such as those described above. In another aspect, the variant further comprises or consists of substitutions at positions corresponding to positions 245 and 420, such as those described above. In another aspect, the variant further comprises or consists of substitutions at positions corresponding to positions 382 and 420, such as those described above. In another aspect, the variant further comprises or consists of substitutions at positions corresponding to positions 420 and 440, such as those described above. In another aspect, the variant further comprises or consists of a substitution at positions corresponding to positions 245 and 437, such as those described above. In another aspect, the variant further comprises or consists of substitutions at positions corresponding to positions 382 and 437, such as those described above. In another aspect, the variant further comprises or consists of substitutions at positions corresponding to positions 437 and 440, such as those described above. In another aspect, the variant further comprises or consists of a substitution at positions corresponding to positions 245 and 382, such as those described above. In another aspect, the variant further comprises or consists of a substitution at positions corresponding to positions 245 and 440, such as those described above. In another aspect, the variant further comprises or consists of a substitution at positions corresponding to positions 382 and 440, such as those described above.

In another aspect, the variant further comprises or consists of any two substitutions selected from A245S, G382C, L420I, T437Q, and Q440C corresponding to SEQ ID NO: 2. In one aspect, the variant further comprises or consists of the substitutions L420I+T437Q corresponding to SEQ ID NO: 2. In another aspect, the variant further comprises or consists of the substitutions A245S+L420I. In another aspect, the variant further comprises or consists of the substitutions G382C+L420I. In another aspect, the variant further comprises or consists of the substitutions L420I+Q440C. In another aspect, the variant further comprises or consists of the substitutions A245S+T437Q. In another aspect, the variant further comprises or consists of the substitutions G382C+T437Q. In another aspect, the variant further comprises or consists of the substitutions T437Q+Q440C. In another aspect, the variant further comprises or consists of the substitutions A245S+G382C. In another aspect, the variant further comprises or consists of the substitutions A245S+Q440C. In another aspect, the variant further comprises or consists of the substitutions G382C+Q440C.

In one aspect, the variant further comprises or consists of substitutions at any three positions corresponding to positions 245, 382, 420, 437, and 440 of SEQ ID NO: 2, such as those described above. In one aspect, the variant further comprises or consists of a substitution at positions corresponding to positions 245, 420, and 437 of SEQ ID NO: 2, such as those described above. In another aspect, the variant further comprises or consists of a substitution at positions corresponding to positions 382, 420, and 437, such as those described above.

In another aspect, the variant further comprises or consists of a substitution at positions corresponding to positions 420, 437, and 440, such as those described above. In another aspect, the variant further comprises or consists of a substitution at positions corresponding to positions 245, 382, and 420 such as those described above. In another aspect, the variant further comprises or consists of a substitution at positions corresponding to positions 245, 420, and 440, such as those described above. In another aspect, the variant further comprises or consists of a substitution at positions corresponding to positions 382, 420, and 440, such as those described above. In another aspect, the variant further comprises or consists of a substitution at positions corresponding to positions 245, 382, and 437, such as those described above. In another aspect, the variant further comprises or consists of a substitution at positions corresponding to positions 245, 437, and 440, such as those described above. In another aspect, the variant further comprises or consists of a substitution at positions corresponding to positions 382, 437, and 440, such as those described above. In another aspect, the variant further comprises or consists of a substitution at positions corresponding to positions 245, 382, and 440, such as those described above.

In another aspect, the variant further comprises or consists of any three substitutions selected from A245S, G382C, L420I, T437Q, and Q440C corresponding to SEQ ID NO: 2. In one aspect, the variant further comprises or consists of the substitutions A245S+L420I+T437Q corresponding to SEQ ID NO: 2. In another aspect, the variant further comprises or consists of the substitutions G382C+L420I+T437Q. In another aspect, the variant further comprises or consists of the substitutions L420I+T437Q+Q440C. In another aspect, the variant further comprises or consists of the substitutions A245S+G382C+L420I. In another aspect, the variant further comprises or consists of the substitutions A245S+L420I+Q440C. In another aspect, the variant further comprises or consists of the substitutions G382C+L420I+Q440C. In another aspect, the variant further comprises or consists of the substitutions A245S+G382C+T437Q. In another aspect, the variant further comprises or consists of the substitutions A245S+T437Q+Q440C. In another aspect, the variant further comprises or consists of the substitutions G382C+T437Q+Q440C. In another aspect, the variant further comprises or consists of the substitutions A245S+G382C+Q440C.

In one aspect, the variant further comprises or consists of substitutions at any four positions corresponding to positions 245, 382, 420, 437, and 440 of SEQ ID NO: 2, such as those described above. In one aspect, the variant further comprises or consists of a substitution at positions corresponding to positions 245, 382, 437, and 440 of the mature polypeptide of SEQ ID NO: 2, such as those described above. In another aspect, the variant further comprises or consists of a substitution at positions corresponding to positions 245, 382, 420, and 440, such as those described above. In another aspect, the variant further comprises or consists of a substitution at positions corresponding to positions 382, 420, 437, and 440, such as those described above. In another aspect, the variant further comprises or consists of a substitution at positions corresponding to positions 245, 420, 437, and 440, such as those described above. In another aspect, the variant further comprises or consists of a substitution at positions corresponding to positions 245, 382, 420, and 437, such as those described above.

In another aspect, the variant further comprises or consists of any four substitutions selected from A245S, G382C, L420I, T437Q, and Q440C corresponding to SEQ ID NO: 2. In one aspect, the variant further comprises or consists of the substitutions A245S+G382C+T437Q+Q440C of the corresponding to SEQ ID NO: 2. In another aspect, the variant further comprises or consists of the substitutions A245S+G382C+L420I+Q440C. In another aspect, the variant further comprises or consists of the substitutions G382C+L420I+T437Q+Q440C. In another aspect, the variant further comprises or consists of the substitutions A245S+L420I+T437Q+Q440C. In another aspect, the variant further comprises or consists of the substitutions A245S+G382C+L420I+T437Q.

In one aspect, the variant further comprises or consists of a substitution at positions corresponding to positions 245, 382, 420, 437, and 440 of SEQ ID NO: 2, such as those described above. In one aspect, the variant further comprises or consists of the substitutions A245S+G382C+L420I+T437Q+Q440C corresponding to SEQ ID NO: 2.

Essential amino acids in a parent can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cellobiohydrolase activity to identify amino acid residues that are critical to the activity of the molecule. See also, Hilton et al., 1996, *J. Biol. Chem.* 271: 4699-4708. The active site of the cellobiohydrolase or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the parent.

The variants may consist of 370 to 450 amino acids, e.g., 370 to 379, 380 to 389, 390 to 399, 400 to 409, 410 to 419, and 420 to 440 amino acids.

The invention also encompasses polypeptides having cellobiohydrolase activity, wherein one or more (several) positions of the amino acid sequence differ from corresponding positions 254, 285, 286, 330, 342, and 360 of SEQ ID NO: 2. The variant aspects described herein also embrace similar aspects related to polypeptides having cellobiohydrolase activity.

Polynucleotides

The present invention also relates to isolated polynucleotides that encode any of the variants of the present invention.

Nucleic Acid Constructs

The present invention also relates to nucleic acid constructs comprising a polynucleotide encoding a variant of the present invention operably linked to one or more (several) control sequences that direct the expression of the coding sequence in a suitable host cell under conditions compatible with the control sequences.

A polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, which is recognized by a host cell for expression of the polynucleotide. The promoter sequence contains transcriptional control sequences that mediate the expression of the variant. The promoter may be any nucleic acid sequence that shows transcriptional activity in the host cell including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra.

Examples of suitable promoters for directing the transcription of the nucleic acid constructs of the present invention in a filamentous fungal host cell are the promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in *Aspergilli* in which the untranslated leader has been replaced by an untranslated leader from a gene encoding triose phosphate isomerase in *Aspergilli*; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the variant. Any terminator that is functional in the host cell may be used.

Preferred terminators for filamentous fungal host cells are obtained from the genes for *Aspergillus nidulans* anthranilate synthase, *Aspergillus niger* alpha-glucosidase, *Aspergillus niger* glucoamylase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5'-terminus of the polynucleotide encoding the variant. Any leader sequence that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding region naturally linked in translation reading frame with the segment of the coding region that encodes the variant. Alternatively, the 5'-end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the variant. However, any signal peptide coding region that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding region that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide regions are present at the N-terminus of a variant, the propeptide region is positioned next to the N-terminus of the variant and the signal peptide region is positioned next to the N-terminus of the propeptide region.

It may also be desirable to add regulatory sequences that allow the regulation of the expression of the variant relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about the expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus licheniformis* or *Bacillus subtilis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra) to obtain isolated variants.

Host Cells

The present invention also relates to recombinant host cells, comprising a polynucleotide of the present invention operably linked to one or more (several) control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any gram-positive or gram-negative bacterium. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell, including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell, including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell, including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

The yeast host cell may be a *Candida*, *Hansenula*, *Kluyveromyces*, *Pichia*, *Saccharomyces*, *Schizosaccharomyces*, or *Yarrowia* cell such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus Fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell. In one aspect, the host cell is an *Aspergillus,* e.g., *Aspergillus oryzae.*

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for the expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods may include use of specific antibodies, formation of an enzyme product, or disappearance of an enzyme substrate. For example, an enzyme assay may be used to determine the activity of the variant.

The variant may be recovered by methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification,* J.-C. Janson and Lars Ryden, editors, VCH Publishers, New York, 1989) to obtain isolated variants.

In an alternative aspect, the variant is not recovered, but rather a host cell of the present invention expressing a variant is used as a source of the variant.

Compositions

The present invention also relates to compositions comprising a variant of the present invention. Preferably, the compositions are enriched in such a variant. The term "enriched" means that the cellobiohydrolase activity of the composition has been increased, e.g., with an enrichment factor of 1.1.

The composition may comprise a variant as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus,* e.g., *Aspergillus aculeatus, Aspergillus awamori, Aspergillus foetidus, Aspergillus Fumigatus, Aspergillus japonicus, Aspergillus nidulans, Aspergillus niger,* or *Aspergillus oryzae; Fusarium,* e.g., *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum; Humicola,* e.g., *Humicola insolens* or *Humicola lanuginosa;* or *Trichoderma,* e.g., *Trichoderma harzianum, Trichoderma koningii, Trichoderma longibrachiatum, Trichoderma reesei,* or *Trichoderma viride.*

The compositions may be prepared in accordance with methods known in the art and may be in the form of a liquid or a dry composition. For instance, the composition may be in the form of a granulate or a microgranulate. The variant may be stabilized in accordance with methods known in the art.

Processing of Cellulosic Material

The present invention also relates to methods for degrading or converting a cellulosic material, comprising: treating the cellulosic material with an enzyme composition in the presence of a variant having cellobiohydrolase activity of the present invention. In a preferred aspect, the method further comprises recovering the degraded or converted cellulosic material.

The present invention also relates to methods of producing a fermentation product, comprising: (a) saccharifying a cellulosic material with an enzyme composition in the presence of a variant having cellobiohydrolase activity of the present invention; (b) fermenting the saccharified cellulosic material with one or more (several) fermenting microorganisms to produce the fermentation product; and (c) recovering the fermentation product from the fermentation.

The present invention also relates to methods of fermenting a cellulosic material, comprising: fermenting the cellulosic material with one or more (several) fermenting microorganisms, wherein the cellulosic material is saccharified with an enzyme composition in the presence of a variant having cellobiohydrolase activity of the present invention. In a preferred aspect, the fermenting of the cellulosic material produces a fermentation product. In another preferred aspect, the method further comprises recovering the fermentation product from the fermentation.

The methods of the present invention can be used to saccharify a cellulosic material to fermentable sugars and convert the fermentable sugars to many useful substances, e.g., fuel, potable ethanol, and/or fermentation products (e.g., acids, alcohols, ketones, gases, and the like). The production of a desired fermentation product from cellulosic material typically involves pretreatment, enzymatic hydrolysis (saccharification), and fermentation.

The processing of cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and cofermentation (SSCF); hybrid hydrolysis and fermentation (HHF); separate hydrolysis and co-fermentation (SHCF); hybrid hydrolysis and fermentation (HHCF); and direct microbial conversion (DMC). SHF uses separate process steps to first enzymatically hydrolyze cellulosic material to fermentable sugars, e.g., glucose, cellobiose, cellotriose, and pentose sugars, and then ferment the fermentable sugars to ethanol. In SSF, the enzymatic hydrolysis of cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include: fluidized bed, upflow blanket, immobilized, and extruder type reactors for hydrolysis and/or fermentation.

Pretreatment. In practicing the methods of the present invention, any pretreatment process known in the art can be used to disrupt plant cell wall components of cellulosic material (Chandra et al., 2007, Substrate pretreatment: The key to effective enzymatic hydrolysis of lignocellulosics? *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, pre-soaking, wetting, washing, or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, cellulosic material is heated to disrupt the plant cell wall components, including lignin, hemicellulose, and cellulose to make the cellulose and other fractions, e.g., hemicellulose, accessible to enzymes. Cellulosic material is passed to or through a reaction vessel where steam is injected to increase the temperature to the required temperature and pressure and is retained therein for the desired reaction time. Steam pretreatment is preferably done at 140-230° C., more preferably 160-200° C., and most preferably 170-190° C., where the optimal temperature range depends on any addition of a chemical catalyst. Residence time for the steam pretreatment is preferably 1-15 minutes, more preferably 3-12 minutes, and most preferably 4-10 minutes, where the optimal residence time depends on temperature range and any addition of a chemical catalyst. Steam pretreatment allows for relatively high solids loadings, so that cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

A catalyst such as $H_2SO_4$ or $SO_2$ (typically 0.3 to 3% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/11899, WO 2006/11900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating cellulosic material with liquid or gaseous ammonia at moderate temperatures such as 90-100° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). AFEX pretreatment results in the depolymerization of cellulose and partial hydrolysis of hemicellulose. Lignin-carbohydrate complexes are cleaved.

Organosolv pretreatment delignifies cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as an acid treatment, and more preferably as a continuous dilute and/or mild acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, more preferably 1-4, and most preferably 1-3. In one aspect, the acid concentration is in the range from preferably 0.01 to 20 wt % acid, more preferably 0.05 to 10 wt % acid, even more preferably 0.1 to 5 wt % acid, and most preferably 0.2 to 2.0 wt % acid. The acid is contacted with cellulosic material and held at a temperature in the range of preferably 160-220° C., and more preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In preferred aspects, cellulosic material is present during pretreatment in amounts preferably between 10-80 wt %, more preferably between 20-70 wt %, and most preferably between 30-60 wt %, such as around 50 wt %. The pretreated cellulosic material can be unwashed or washed using any method known in the art, e.g., washed with water.

Mechanical Pretreatment: The term "mechanical pretreatment" refers to various types of grinding or milling (e.g., dry milling, wet milling, or vibratory ball milling).

Physical Pretreatment: The term "physical pretreatment" refers to any pretreatment that promotes the separation and/or release of cellulose, hemicellulose, and/or lignin from cellulosic material. For example, physical pretreatment can involve irradiation (e.g., microwave irradiation), steaming/steam explosion, hydrothermolysis, and combinations thereof.

Physical pretreatment can involve high pressure and/or high temperature (steam explosion). In one aspect, high pressure means pressure in the range of preferably about 300 to about 600 psi, more preferably about 350 to about 550 psi, and most preferably about 400 to about 500 psi, such as around 450 psi. In another aspect, high temperature means temperatures in the range of about 100 to about 300° C., preferably about 140 to about 235° C. In a preferred aspect, mechanical pretreatment is performed in a batch-process, steam gun hydrolyzer system that uses high pressure and high temperature as defined above, e.g., a Sunds Hydrolyzer available from Sunds Defibrator AB, Sweden.

Combined Physical and Chemical Pretreatment: Cellulosic material can be pretreated both physically and chemically. For instance, the pretreatment step can involve dilute or mild acid treatment and high temperature and/or pressure treatment. The physical and chemical pretreatments can be carried out sequentially or simultaneously, as desired. A mechanical pretreatment can also be included.

Accordingly, in a preferred aspect, cellulosic material is subjected to mechanical, chemical, or physical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from cellulosic material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and alternatively also hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a variant having cellobiohydrolase activity of the present invention. The composition can further comprise one or more (several) hemicellulolytic or xylan degrading enzymes. The enzymes of the compositions can also be added sequentially.

Enzymatic hydrolysis is preferably carried out in a suitable aqueous environment under conditions that can be readily determined by one skilled in the art. In a preferred aspect, hydrolysis is performed under conditions suitable for the activity of the enzyme(s), i.e., optimal for the enzyme(s). The hydrolysis can be carried out as a fed batch or continuous process where the cellulosic material (substrate), e.g., pretreated, is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 96 hours, more preferably about 16 to about 72 hours, and most preferably about 24 to about 48 hours. The temperature is in the range of preferably about 25° C. to about 70° C., more preferably about 30° C. to about 65° C., and more preferably about 40° C. to 60° C., in particular about 50° C. The pH is in the range of preferably about 3 to about 8, more preferably about 3.5 to about 7, and most preferably about 4 to about 6, in particular about pH 5. The dry solids content is in the range of preferably about 5 to about 50 wt %, more preferably about 10 to about 40 wt %, and most preferably about 20 to about 30 wt %.

The enzyme composition preferably comprises enzymes having cellulolytic activity and/or xylan degrading activity. In one aspect, the enzyme composition comprises one or more (several) cellulolytic enzymes. In another aspect, the enzyme composition comprises one or more (several) xylan degrading enzymes. In another aspect, the enzyme composition comprises one or more (several) cellulolytic enzymes and one or more (several) xylan degrading enzymes.

The one or more (several) cellulolytic enzymes are preferably selected from the group consisting of an endoglucanase, a cellobiohydrolase, and a beta-glucosidase. The one or more (several) xylan degrading enzymes are preferably selected from the group consisting of a xylanase, an acetyxylan esterase, a feruloyl esterase, an arabinofuranosidase, a xylosidase, and a glucuronidase.

In another aspect, the enzyme composition further or even further comprises a polypeptide having cellulolytic enhancing activity (see, for example, WO 2005/074647, WO 2005/074656, and WO 2007/089290). In another aspect, the enzyme composition may further or even further comprise one or more (several) additional enzyme activities to improve the degradation of the cellulose-containing material. Preferred additional enzymes are hemicellulases (e.g., alpha-D-glucuronidases, alpha-L-arabinofuranosidases, endo-mannanases, beta-mannosidases, alpha-galactosidases, endo-alpha-L-arabinanases, beta-galactosidases), carbohydrate-esterases (e.g., acetyl-xylan esterases, acetyl-mannan esterases, ferulic acid esterases, coumaric acid esterases, glucuronoyl esterases), pectinases, proteases, ligninolytic enzymes (e.g., laccases, manganese peroxidases, lignin peroxidases, $H_2O_2$-producing enzymes, oxidoreductases), expansins, swollenins, or mixtures thereof. In the methods of the present invention, the additional enzyme(s) can be added prior to or during fermentation, e.g., during saccharification or during or after propagation of the fermenting microorganism(s).

One or more (several) components of the enzyme composition may be wild-type proteins, recombinant proteins, or a combination of wild-type proteins and recombinant proteins. For example, one or more (several) components may be native proteins of a cell, which is used as a host cell to express recombinantly one or more (several) other components of the enzyme composition. One or more (several) components of the enzyme composition may be produced as monocomponents, which are then combined to form the enzyme composition. The enzyme composition may be a combination of multicomponent and monocomponent protein preparations.

The enzymes used in the methods of the present invention may be in any form suitable for use in the processes described herein, such as, for example, a crude fermentation broth with or without cells removed, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and variants having cellobiohydrolase activity depend on several factors including, but not limited to, the mixture of component cellulolytic enzymes, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation).

In a preferred aspect, an effective amount of cellulolytic enzyme(s) to cellulosic material is about 0.5 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulosic material.

In another preferred aspect, an effective amount of a variant having cellobiohydrolase activity to cellulosic material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably at about 0.025 to about 1.5 mg, more preferably at about 0.05 to about 1.25 mg, more preferably at about 0.075 to about 1.25 mg, more preferably at about 0.1 to about 1.25 mg, even more preferably at about 0.15 to about 1.25 mg, and most preferably at about 0.25 to about 1.0 mg per g of cellulosic material.

In another preferred aspect, an effective amount of a variant having cellobiohydrolase activity to cellulolytic enzyme(s) is about 0.005 to about 1.0 g, preferably at about 0.01 to about 1.0 g, more preferably at about 0.15 to about 0.75 g, more preferably at about 0.15 to about 0.5 g, more preferably at about 0.1 to about 0.5 g, even more preferably at about 0.1 to about 0.5 g, and most preferably at about 0.05 to about 0.2 g per g of cellulolytic enzyme(s).

The enzymes can be derived or obtained from any suitable origin, including, bacterial, fungal, yeast, plant, or mammalian origin. The term "obtained" means herein that the enzyme may have been isolated from an organism that naturally produces the enzyme as a native enzyme. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having cellulolytic enzyme activity or xylan degrading activity may be a bacterial polypeptide. For example, the polypeptide may be a gram positive bacterial polypeptide such as a *Bacillus*, *Streptococcus*, *Streptomyces*, *Staphylococcus*, *Enterococcus*, *Lactobacillus*, *Lactococcus*, *Clostridium*, *Geobacillus*, or *Oceanobacillus* polypeptide having cellulolytic enzyme activity or xylan degrading activity, or a Gram negative bacterial polypeptide such as an *E. coli*, *Pseudomonas*, *Salmonella*, *Campylobacter*, *Helicobacter*, *Flavobacterium*, *Fusobacterium*, *Ilyobacter*, *Neisseria*, or *Ureaplasma* polypeptide having cellulolytic enzyme activity or xylan degrading activity.

In a preferred aspect, the polypeptide is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* polypeptide having cellulolytic enzyme activity or xylan degrading activity.

In another preferred aspect, the polypeptide is a *Streptococcus equisimilis*, *Streptococcus pyogenes*, *Streptococcus uberis*, or *Streptococcus equi* subsp. *Zooepidemicus* polypeptide having cellulolytic enzyme activity or xylan degrading activity.

In another preferred aspect, the polypeptide is a *Streptomyces achromogenes*, *Streptomyces avermitilis*, *Streptomyces coelicolor*, *Streptomyces griseus*, or *Streptomyces lividans* polypeptide having cellulolytic enzyme activity or xylan degrading activity.

The polypeptide having cellulolytic enzyme activity or xylan degrading activity may also be a fungal polypeptide, and more preferably a yeast polypeptide such as a *Candida*, *Kluyveromyces*, *Pichia*, *Saccharomyces*, *Schizosaccharomyces*, or *Yarrowia* polypeptide having cellulolytic enzyme activity or xylan degrading activity; or more preferably a filamentous fungal polypeptide such as an *Acremonium*, *Agaricus*, *Alternaria*, *Aspergillus*, *Aureobasidium*, *Botryospaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*,

*Talaromyces, Thermoascus, Thielavia, Tolypocladium, Trichoderma, Trichophaea, Verticillium, Volvariella,* or *Xylaria* polypeptide having cellulolytic enzyme activity or xylan degrading activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having cellulolytic enzyme activity or xylan degrading activity.

In another preferred aspect, the polypeptide is an *Acremonium cellulolyticus, Aspergillus* aculeatus, *Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having cellulolytic enzyme activity or xylan degrading activity.

Chemically modified or protein engineered mutants of polypeptides having cellulolytic enzyme activity or xylan degrading activity may also be used.

One or more (several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

Examples of commercial cellulolytic protein preparations suitable for use in the present invention include, for example, CELLIC™ Ctec (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, more preferably from about 0.025 to about 4.0 wt % of solids, and most preferably from about 0.005 to about 2.0 wt % of solids. The cellulase enzymes are added in amounts effective from about 0.001 to about 5.0 wt % of solids, more preferably from about 0.025 to about 4.0 wt % of solids, and most preferably from about 0.005 to about 2.0 wt % of solids.

Examples of bacterial endoglucanases that can be used in the methods of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the methods of the present invention, include, but are not limited to, a *Trichoderma reesei* endoglucanase I (Penttila et al., 1986, *Gene* 45: 253-263; GENBANK™ accession no. M15665); *Trichoderma reesei* endoglucanase II (Saloheimo, et al., 1988, *Gene* 63:11-22; GENBANK™ accession no. M19373); *Trichoderma reesei* endoglucanase III (Okada et al., 1988, *Appl. Environ. Microbiol.* 64: 555-563; GENBANK™ accession no. AB003694); and *Trichoderma reesei* endoglucanase V (Saloheimo et al., 1994, *Molecular Microbiology* 13: 219-228; GENBANK™ accession no. Z33381); *Aspergillus aculeatus* endoglucanase (Ooi et al., 1990, *Nucleic Acids Research* 18: 5884); *Aspergillus kawachii* endoglucanase (Sakamoto et al., 1995, *Current Genetics* 27: 435-439); *Erwinia carotovara* endoglucanase (Saarilahti et al., 1990, *Gene* 90: 9-14); *Fusarium oxysporum* endoglucanase (GENBANK™ accession no. L29381); *Humicola grisea* var. *thermoidea* endoglucanase (GENBANK™ accession no. AB003107); *Melanocarpus albomyces* endoglucanase (GENBANK™ accession no. MAL515703); *Neurospora crassa* endoglucanase (GENBANK™ accession no. XM_324477); *Humicola insolens* endoglucanase V; *Myceliophthora thermophila* CBS 117.65 endoglucanase; basidiomycete CBS 495.95 endoglucanase; basidiomycete CBS 494.95 endoglucanase; *Thielavia terrestris* NRRL 8126 CEL6B endoglucanase; *Thielavia terrestris* NRRL 8126 CEL6C endoglucanase); *Thielavia terrestris* NRRL 8126 CEL7C endoglucanase; *Thielavia terrestris* NRRL 8126 CEL7E endoglucanase; *Thielavia terrestris* NRRL 8126 CEL7F endoglucanase; *Cladorrhinum foecundissimum* ATCC 62373 CEL7A endoglucanase; and *Trichoderma reesei* strain No. VTT-D-80133 endoglucanase (GENBANK™ accession no. M15665).

Examples of cellobiohydrolases useful in the methods of the present invention include, but are not limited to, *Trichoderma reesei* cellobiohydrolase I; *Trichoderma reesei* cellobiohydrolase II; *Humicola insolens* cellobiohydrolase I, *Myceliophthora thermophila* cellobiohydrolase II, *Thielavia terrestris* cellobiohydrolase II (CEL6A), *Chaetomium thermophilum* cellobiohydrolase I, and *Chaetomium thermophilum* cellobiohydrolase II.

Examples of beta-glucosidases useful in the methods of the present invention include, but are not limited to, *Aspergillus oryzae* beta-glucosidase; *Aspergillus fumigatus* beta-glucosidase; *Penicillium brasilianum* IBT 20888 beta-glucosidase; *Aspergillus niger* beta-glucosidase; and *Aspergillus aculeatus* beta-glucosidase.

The *Aspergillus oryzae* polypeptide having beta-glucosidase activity can be obtained according to WO 2002/095014. The *Aspergillus fumigatus* polypeptide having beta-glucosidase activity can be obtained according to WO 2005/047499. The *Penicillium* brasilianum polypeptide having beta-glucosidase activity can be obtained according to WO 2007/019442. The *Aspergillus niger* polypeptide having beta-glucosidase activity can be obtained according to Dan et al., 2000, *J. Biol. Chem.* 275: 4973-4980. The *Aspergillus* aculeatus polypeptide having beta-glucosidase activity can be obtained according to Kawaguchi et al., 1996, *Gene* 173: 287-288.

The beta-glucosidase may be a fusion protein. In one aspect, the beta-glucosidase is the *Aspergillus oryzae* beta-glucosidase variant BG fusion protein or the *Aspergillus oryzae* beta-glucosidase fusion protein obtained according to WO 2008/057637.

Other endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in EP 495,257, EP 531,315, EP 531,372, WO 89/09259, WO 94/07998, WO 95/24471, WO 96/11262, WO 96/29397, WO 96/034108, WO 97/14804, WO 98/08940, WO 98/012307, WO 98/13465, WO 98/015619, WO 98/015633, WO 98/028411, WO 99/06574, WO 99/10481, WO 99/025846, WO 99/025847, WO 99/031255, WO 2000/009707, WO 2002/050245, WO 2002/0076792, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 4,435,307, U.S. Pat. No. 5,457,046, U.S. Pat. No. 5,648,263, U.S. Pat. No. 5,686,593, U.S. Pat. No. 5,691,178, U.S. Pat. No. 5,763,254, and U.S. Pat. No. 5,776,757.

In the methods of the present invention, any polypeptide having cellulolytic enhancing activity can be used.

In a first aspect, the polypeptide having cellulolytic enhancing activity comprises the following motifs:

[ILMV]-P-X(4,5)-G-X-Y-[ILMV]-X-R-X-[EQ]-X(4)-[HNQ] and [FW]-[TF]-K-[AIV], wherein X is any amino acid, X(4,5) is any amino acid at 4 or 5 contiguous positions, and X(4) is any amino acid at 4 contiguous positions.

The polypeptide comprising the above-noted motifs may further comprise:

H-X(1,2)-G-P-X(3)-[YW]-[AILMV],

[EQ]-X-Y-X(2)-C-X-[EHQN]-[FILV]-X-[ILV], or

H-X(1,2)-G-P-X(3)-[YW]-[AILMV] and [EQ]-X-Y-X(2)-C-X-[EHQN]-[FILV]-X-[ILV], wherein X is any amino acid, X(1,2) is any amino acid at 1 position or 2 contiguous positions, X(3) is any amino acid at 3 contiguous positions, and X(2) is any amino acid at 2 contiguous positions. In the above motifs, the accepted IUPAC single letter amino acid abbreviation is employed.

In a preferred aspect, the polypeptide having cellulolytic enhancing activity further comprises H-X(1,2)-G-P-X(3)-[YW]-[AILMV]. In another preferred aspect, the isolated polypeptide having cellulolytic enhancing activity further comprises [EQ]-X-Y-X(2)-C-X-[EHQN]-[FILV]-X-[ILV]. In another preferred aspect, the polypeptide having cellulolytic enhancing activity further comprises H-X(1,2)-G-P-X(3)-[YW]-[AILMV] and [EQ]-X-Y-X(2)-C-X-[EHQN]-[FILV]-X-[ILV].

In a second aspect, the polypeptide having cellulolytic enhancing activity comprises the following motif:

[ILMV]-P-x(4,5)-G-x-Y-[ILMV]-x-R-x-[EQ]-x(3)-A-[HNQ], wherein x is any amino acid, x(4,5) is any amino acid at 4 or 5 contiguous positions, and x(3) is any amino acid at 3 contiguous positions. In the above motif, the accepted IUPAC single letter amino acid abbreviation is employed.

Examples of polypeptides having cellulolytic enhancing activity useful in the methods of the present invention include, but are not limited to, polypeptides having cellulolytic enhancing activity from *Thielavia terrestris* (WO 2005/074647); polypeptides having cellulolytic enhancing activity from *Thermoascus aurantiacus* (WO 2005/074656); and polypeptides having cellulolytic enhancing activity from *Trichoderma reesei* (WO 2007/089290).

Examples of commercial xylan degrading enzyme preparations suitable for use in the present invention include, for example, SHEARZYME™ (Novozymes A/S), CELLIC™ Htec (Novozymes A/S), VISCOZYME® (Novozymes A/S), ULTRAFLO® (Novozymes A/S), PULPZYME® HC (Novozymes A/S), MULTIFECT® Xylanase (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the methods of the present invention include, but are not limited to, *Aspergillus aculeatus* xylanase (GeneSeqP:AAR63790; WO 94/21785), *Aspergillus fumigatus* xylanases (WO 2006/078256), and *Thielavia terrestris* NRRL 8126 xylanases (WO 2009/079210).

Examples of beta-xylosidases useful in the methods of the present invention include, but are not limited to, *Trichoderma reesei* beta-xylosidase (UniProtKB/TrEMBL accession number Q92458), *Talaromyces emersonii* (SwissProt accession number Q8x212), and *Neurospora crassa* (SwissProt accession number Q7SOW4).

Examples of acetylxylan esterases useful in the methods of the present invention include, but are not limited to, *Hypocrea jecorina* acetylxylan esterase (WO 2005/001036), *Neurospora crassa* acetylxylan esterase (UniProt accession number q7s259), *Thielavia terrestris* NRRL 8126 acetylxylan esterase (WO 2009/042846), *Chaetomium globosum* acetylxylan esterase (Uniprot accession number Q2GWX4), *Chaetomium gracile* acetylxylan esterase (GeneSeqP accession number AAB82124), *Phaeosphaeria nodorum* acetylxylan esterase (Uniprot accession number Q0UHJ1), and *Humicola insolens* DSM 1800 acetylxylan esterase (WO 2009/073709).

Examples of ferulic acid esterases useful in the methods of the present invention include, but are not limited to, *Humicola insolens* DSM 1800 feruloyl esterase (WO 2009/076122), *Neurospora crassa* feruloyl esterase (UniProt accession number Q9HGR3), and *Neosartorya fischeri* feruloyl esterase (UniProt Accession number A1D9T4).

Examples of arabinofuranosidases useful in the methods of the present invention include, but are not limited to, *Humicola insolens* DSM 1800 arabinofuranosidase (WO 2009/073383) and *Aspergillus niger* arabinofuranosidase (GeneSeqP accession number AAR94170).

Examples of alpha-glucuronidases useful in the methods of the present invention include, but are not limited to, *Aspergillus clavatus* alpha-glucuronidase (UniProt accession number alcc12), *Trichoderma reesei* alpha-glucuronidase (Uniprot accession number Q99024), *Talaromyces emersonii* alpha-glucuronidase (UniProt accession number Q8x211),

*Aspergillus niger* alpha-glucuronidase (Uniprot accession number Q96WX9), *Aspergillus terreus* alpha-glucuronidase (SwissProt accession number Q0CJP9), and *Aspergillus fumigatus* alpha-glucuronidase (SwissProt accession number Q4WW45).

The enzymes and proteins used in the methods of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be $C_6$ and/or $C_5$ fermenting organisms, or a combination thereof. Both $C_6$ and $C_5$ fermenting organisms are well known in the art. Suitable fermenting microorganisms are able to ferment, i.e., convert, sugars, such as glucose, xylose, xylulose, arabinose, maltose, mannose, galactose, or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment $C_6$ sugars include bacterial and fungal organisms, such as yeast. Preferred yeast includes strains of the *Saccharomyces* spp., preferably *Saccharomyces cerevisiae*.

Examples of fermenting organisms that can ferment $C_5$ sugars include bacterial and fungal organisms, such as yeast. Preferred $C_5$ fermenting yeast include strains of *Pichia*, preferably *Pichia stipitis*, such as *Pichia stipitis* CBS 5773; strains of *Candida*, preferably *Candida boidinii*, *Candida brassicae*, *Candida sheatae*, *Candida diddensii*, *Candida pseudotropicalis*, or *Candida utilis*.

Other fermenting organisms include strains of *Zymomonas*, such as *Zymomonas mobilis*; *Hansenula*, such as *Hansenula anomala*; *Kluyveromyces*, such as *K. fragilis*; *Schizosaccharomyces*, such as *S. pombe*; and *E. coli*, especially *E. coli* strains that have been genetically modified to improve the yield of ethanol.

In a preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyveromyces fragilis*. In another preferred aspect, the yeast is a *Candida*. In another more preferred aspect, the yeast is *Candida boidinii*. In another more preferred aspect, the yeast is *Candida brassicae*. In another more preferred aspect, the yeast is *Candida diddensii*. In another more preferred aspect, the yeast is *Candida pseudotropicalis*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment hexose and pentose to ethanol include, for example, *Zymomonas mobilis* and *Clostridium thermocellum* (Philippidis, 1996, supra).

In a preferred aspect, the bacterium is a *Zymomonas*. In a more preferred aspect, the bacterium is *Zymomonas mobilis*. In another preferred aspect, the bacterium is a *Clostridium*. In another more preferred aspect, the bacterium is *Clostridium thermocellum*.

Commercially available yeast suitable for ethanol production includes, e.g., ETHANOL RED™ yeast (available from Fermentis/Lesaffre, USA), FALI™ (available from Fleischmann's Yeast, USA), SUPERSTART™ and THERMOSACC™ fresh yeast (available from Ethanol Technology, WI, USA), BIOFERM™ AFT and XR (available from NABC—North American Bioproducts Corporation, GA, USA), GERT STRAND™ (available from Gert Strand AB, Sweden), and FERMIOL™ (available from DSM Specialties).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Saccharomyces cerevisiae*. In another preferred aspect, the genetically modified fermenting microorganism is *Zymomonas mobilis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces* sp.

It is well known in the art that the organisms described above can also be used to produce other substances, as described herein.

The fermenting microorganism is typically added to the degraded lignocellulose or hydrolysate and the fermentation is performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In a preferred aspect, the yeast and/or another microorganism is applied to the degraded cellulosic material and the fermentation is performed for about 12 to about 96 hours, such as typically 24-60 hours. In a preferred aspect, the temperature is preferably between about 20° C. to about 60° C., more preferably about 25° C. to about 50° C., and most preferably about 32° C. to about 50° C., in particular about 32° C. or 50° C., and the pH is generally from about pH 3 to about pH 7, preferably around pH 4-7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth.

Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation products: A fermentation product can be any substance derived from the fermentation. The fermentation product can be, without limitation, an alcohol (e.g., arabinitol, butanol, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); a ketone (e.g., acetone); an amino acid (e.g., aspartic acid, glutamic acid, glycine, lysine, serine, and threonine); and a gas (e.g., methane, hydrogen ($H_2$), carbon dioxide ($CO_2$), and carbon monoxide (CO)). The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

Recovery. The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Plants

The present invention also relates to plants, e.g., a transgenic plant, plant part, or plant cell, comprising a polynucleotide of the present invention so as to express and produce the variant in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seeds coats.

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more (several) expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiol.* 86: 506.

For constitutive expression, the 35S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Mol. Biol.* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct prepared according to the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. Crossing results in the introduction of a transgene into a plant line by cross pollinating a starting line with a donor plant line. Non-limiting examples of such steps are further articulated in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a variant of the present invention comprising: (a) cultivating a transgenic plant or a plant cell comprising a polynucleotide encoding the variant under conditions conducive for production of the variant; and (b) recovering the variant.

The present invention is further described by the following examples that should not be construed as limiting the scope of the invention.

EXAMPLES

Materials

Chemicals used as buffers and substrates were commercial products of at least reagent grade.

Strains

*Aspergillus fumigatus* (NN051616) was used as the source of DNA encoding the Family 6A cellobiohydrolase II. *Aspergillus oryzae* JaL355 (WO 2002/40694) was used for expression of the *Aspergillus fumigatus* cellobiohydrolase II and variants thereof.

Media

PDA plates are composed of 39 grams of potato dextrose agar and deionized water to 1 liter.

MDU2BP medium is composed of 45 g of maltose, 1 g of $MgSO_4 \cdot 7H_2O$, 1 g of NaCl, 2 g of $K_2SO_4$, 12 g of $KH_2PO_4$, 7 g of yeast extract, 2 g of urea, 0.5 ml of AMG trace metals solution, and deionized water to 1 liter; pH to 5.0.

AMG trace metals solution is composed of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, 3 g of citric acid, and deionized water to 1 liter.

LB medium is composed of 10 g of tryptone, 5 g of yeast extract, 5 g of sodium chloride, and deionized water to 1 liter.

2×YT plates are composed of 16 g of tryptone, 10 g of yeast extract, 5 g of NaCl, 15 g of Noble agar, and deionized water to 1 liter.

Example 1

Aspergillus fumigatus Genomic DNA Extraction

Aspergillus fumigatus was grown in 250 ml of potato dextrose medium in a baffled shake flask at 37° C. and 240 rpm. Mycelia were harvested by filtration, washed twice in 10 mM Tris-1 mM EDTA (TE) buffer (and frozen under liquid nitrogen). Frozen mycelia were ground, by mortar and pestle, to a fine powder, which was resuspended in pH 8.0 buffer containing 10 mM Tris, 100 mM EDTA, 1% Triton X-100, 0.5 M guanidine-HCl, and 200 mM NaCl. DNase free RNase A was added at a concentration of 20 mg/liter and the lysate was incubated at 37° C. for 30 minutes. Cellular debris was removed by centrifugation, and DNA was isolated by using a QIAGEN® Maxi 500 column (QIAGEN Inc., Valencia, Calif., USA). The columns were equilibrated in 10 ml of QBT washed with 30 ml of QC, and eluted with 15 ml of QF (all buffers from QIAGEN Inc., Valencia, Calif., USA). DNA was precipitated in isopropanol, washed in 70% ethanol, and recovered by centrifugation. The DNA was resuspended in TE buffer.

Example 2

Construction of an Expression Vector for the Aspergillus fumigatus Family GH6A cellobiohydrolase II Gene Two synthetic oligonucleotide primers shown below were designed to PCR amplify a full-length open reading frame of the Aspergillus fumigatus GH6A cellobiohydrolase II from genomic DNA. A TOPO Cloning Kit (Invitrogen, Carlsbad, Calif., USA) was used to clone the PCR product. An IN-FUSION™ Cloning Kit (BD Biosciences, Palo Alto, Calif., USA) was used to clone the fragment into pAILo2 (WO 2004/099228).

```
In-Fusion Forward primer:
                                     (SEQ ID NO: 3)
5'-ACTGGATTTACCATGAAGCACCTTGCATCTTCCATCG-3'

In-Fusion Reverse primer:
                                     (SEQ ID NO: 4)
5'-TCACCTCTAGTTAATTAAAAGGACGGGTTAGCGT-3'
```

Bold letters represent coding sequence. The remaining sequence contains sequence identity compared with the insertion sites of pAILo2.

Fifty picomoles of each of the primers above was used in a PCR reaction containing 500 ng of Aspergillus fumigatus genomic DNA, 1× ThermoPol reaction buffer (New England Biolabs, Ipswich, Mass., USA), 6 µl of a 10 mM blend of dATP, dTTP, dGTP, and dCTP, and 0.1 units of Taq DNA polymerase (New England Biolabs, Ipswich, Mass., USA), in a final volume of 50 µl. The amplification reaction was performed in an EPPENDORF® MASTERCYCLER® 5333 (Eppendorf Scientific, Inc., Westbury, N.Y., USA) programmed for one cycle at 98° C. for 2 minutes; and 35 cycles each at 96° C. for 30 seconds, 61° C. for 30 seconds, and 72° C. for 2 minutes. After the 35 cycles, the reaction was incubated at 72° C. for 10 minutes and then cooled at 10° C. until further processed. To remove the A-tails produced by Taq DNA polymerase the reaction was incubated for 10 minutes at 68° C. in the presence of 1 unit of Pfx DNA polymerase (Invitrogen, Carlsbad, Calif., USA).

A 1.7 kb PCR reaction product was isolated using a 0.8% GTG-agarose gel (Cambrex Bioproducts, East Rutherford, N.J., USA) with 40 mM Tris base-20 mM sodium acetate-1 mM disodium EDTA (TAE) buffer and 0.1 µg of ethidium bromide per ml. The DNA band was visualized with the aid of a DARK READER™ (Clare Chemical Research, Dolores, Colo., USA) to avoid UV-induced mutations. The 1.3 kb DNA band was excised from the gel with a disposable razor blade and purified using an ULTRAFREE®-DA spin cup (Millipore, Billerica, Mass., USA) according to the manufacturer's instructions.

The purified 1.7 kb PCR product was cloned into the vector pCR®4Blunt-TOPO® (Invitrogen, Carlsbad, Calif., USA). Two microliters of the purified PCR product were mixed with 1 µl of a 2 M sodium chloride solution and 1 µl of the TOPO® vector. The reaction was incubated at room temperature for 15 minutes and then 2 µl of the reaction were used to transform TOP10 E. coli competent cells according to the manufacturer's instructions (Invitrogen, Carlsbad, Calif., USA). Two aliquots of 100 µl each of the transformation reaction were spread onto two 150 mm 2×YT plates supplemented with 100 µg of ampicillin per ml and incubated overnight at 37° C.

Eight recombinant colonies were each inoculated into 3 ml of LB medium supplemented with 100 µg of ampicillin per ml. Plasmid DNA was prepared from these cultures using a BIOROBOT® 9600 (QIAGEN Inc., Valencia, Calif., USA). Clones were analyzed by restriction digestion. Plasmid DNA from each clone was digested with the Eco RI and analyzed by 1% agarose gel electrophoresis using TAE buffer. Six out of eight clones had the expected restriction digestion pattern. Clones 2, 4, 5, 6, 7 and 8 were selected to be sequenced to confirm that there were no mutations in the cloned insert. Sequence analysis of their 5-prime and 3-prime ends indicated that clones 2, 6 and 7 had the correct sequence. These three clones were selected for re-cloning into pAILo2. One microliter of each clone was mixed with 17 µl of TE buffer diluted 10-fold and 1 µl of this mix was used to re-amplify the Aspergillus fumigatus GH6A cellobiohydrolase coding region.

Fifty picomoles of each of the primers above were used in a PCR reaction containing 1 µl of the diluted mix of clones 2, 6 and 7, 1× Pfx Amplification Buffer (Invitrogen, Carlsbad, Calif., USA), 6 µl of a 10 mM blend of dATP, dTTP, dGTP, and dCTP, 2.5 units of PLATINUM® Pfx DNA polymerase (Invitrogen, Carlsbad, Calif., USA), and 1 µl of 50 mM $MgSO_4$, in a final volume of 50 µl. An EPPENDORF® MASTERCYCLER® 5333 was used to amplify the fragment programmed for one cycle at 98° C. for 2 minutes; and 35 cycles each at 94° C. for 30 seconds, 61° C. for 30 seconds, and 68° C. for 1.5 minutes. After the 35 cycles, the reaction was incubated at 68° C. for 10 minutes and then cooled at 10° C. until further processed. A 1.3 kb PCR reaction product was isolated using a 0.8% GTG-agarose gel with TAE buffer and 0.1 µg of ethidium bromide per ml. The DNA band was visualized with the aid of a DARK READER™ to avoid UV-induced mutations. The 1.7 kb DNA band was excised from the gel with a disposable razor blade and purified using an ULTRAFREE®-DA spin cup according to the manufacturer's instructions.

Vector pAILo2 was linearized by digestion with Nco I and Pac I. The fragment was purified by agarose gel electrophoresis and ultrafiltration as described above. Cloning of the purified PCR fragment into the linearized and purified pAILo2 vector was performed using an IN-FUSION™ Cloning Kit (BD Biosciences, Palo Alto, Calif., USA). The reaction (20 µl) contained 1×IN-FUSION™ Buffer (BD Biosciences, Palo Alto, Calif., USA), 1×BSA (BD Biosciences, Palo Alto, Calif., USA), 1 µl of IN-FUSION™ enzyme (diluted 1:10) (BD Biosciences, Palo Alto, Calif., USA), 100 ng of pAILo2 digested with Nco I and Pac I, and 50 ng of the *Aspergillus fumigatus* purified 1.7 kb PCR product. The reaction was incubated at room temperature for 30 minutes. A 2 µl sample of the reaction was used to transform TOP10 *E. coli* competent cells according to the manufacturer's instructions. After a recovery period, two 100 µl aliquots from the transformation reaction were plated onto 150 mm 2×YT plates supplemented with 100 µg of ampicillin per ml. The plates were incubated overnight at 37° C. Eight putative recombinant clones was selected at random from the selection plates and plasmid DNA was prepared from each one using a BIOROBOT® 9600. Clones were analyzed by Pst I restriction digestion. Seven out of eight clones had the expected restriction digestion pattern. Clones 1, 2 and 3 were then sequenced to confirm that there were no mutations in the cloned insert. Clone #2 was selected and designated pAILo33.

Example 3

Construction of the *Aspergillus fumigatus* Family GH6A cellobiohydrolase II Gene Variants Variants of the *Aspergillus fumigatus* GH6A cellobiohydrolase II were constructed by performing site-directed mutagenesis on pAILo33 (for pMaWo55, pMaWo 58, pMaWo78, and pAhyG90), or on pAhyG90 (for pMaWo70 and pMaWo71), pMaWo55 (for pMaWo72), pMaWo58 (for pAhyG108), pMaWo70 (for pMaWo73), or pMaWo71 (for pAhyG111) using a QUIKCHANGE® XL Site-Directed Mutagenesis Kit (Stratagene, La Jolla, Calif., USA). A summary of the oligos used for the site-directed mutagenesis and the variants obtained are shown in Table 1.

The resulting variant plasmid DNAs were prepared using a BIOROBOT® 9600. Variant plasmid constructs were sequenced using a 3130xl Genetic Analyzer (Applied Biosystems, Inc., Foster City, Calif., USA) to verify the changes.

TABLE 1

| Amino acid changes | Primer name | Sequences | Cloning Plasmid Name |
|---|---|---|---|
| D330N | MaWo167 | cctacacccagggaAaccccaactgcgacg (SEQ ID NO: 5) | pMaWo55 |
| | MaWo168 | cgtcgcagttggggtTtccctgggtgtagg (SEQ ID NO: 6) | |
| C254L | MaWo173 | gagcgcctacctggagCTtgtcgactatgctctgaagc (SEQ ID NO: 7) | pMaWo58 |
| | MaWo174 | gcttcagagcatagtcgacaAGctccaggtaggcgctc (SEQ ID NO: 8) | |
| M342F | Af cel6a 3f | gaagaagtacatcaacgccTtTgcgcctcttctcaaggaagccg (SEQ ID NO: 9) | pAhyG90 |
| | Af cel6a 3r | cggcttccttgagaagaggcgcAaAggcgttgatgtacttcttc (SEQ ID NO: 10) | |
| M342F + D330N | MaWo167 | cctacacccagggaAaccccaactgcgacg (SEQ ID NO: 5) | pMaWo70 |
| | MaWo168 | cgtcgcagttggggtTtccctgggtgtagg (SEQ ID NO: 6) | |
| M342F + C254L | MaWo173 | gagcgcctacctggagCTtgtcgactatgctctgaagc (SEQ ID NO: 7) | pMaWo71 |
| | MaWo174 | gcttcagagcatagtcgacaAGctccaggtaggcgctc (SEQ ID NO: 8) | |
| C254L + D330N | MaWo173 | gagcgcctacctggagCTtgtcgactatgctctgaagc (SEQ ID NO: 7) | pMaWo72 |
| | MaWo174 | gcttcagagcatagtcgacaAGctccaggtaggcgctc (SEQ ID NO: 8) | |
| C254L + D330N + M342F | MaWo173 | gagcgcctacctggagCTtgtcgactatgctctgaagc (SEQ ID NO: 7) | pMaWo73 |
| | MaWo174 | gcttcagagcatagtcgacaAGctccaggtaggcgctc (SEQ ID NO: 8) | |
| S360G + C254L | MaWo181 | gcccacttcatcatggataccGGGcggaatggcgtccagccc (SEQ ID NO: 11) | pAhyG108 |
| | MaWo182 | gggctggacgccattccgCCCggtatccatgatgaagtgggc (SEQ ID NO: 12) | |
| S360G + C254L + M342F | MaWo181 | gcccacttcatcatggataccGGGcggaatggcgtccagccc (SEQ ID NO: 11) | pAhyG111 |
| | MaWo182 | gggctggacgccattccgCCCggtatccatgatgaagtgggc (SEQ ID NO: 12) | |

TABLE 1-continued

| Amino acid changes | Primer name | Sequences | Cloning Plasmid Name |
|---|---|---|---|
| L285I + G286Q | MaWo205 | ggctcggatggcccgccaacAtCCAAccgccgcaacactcttcgcc (SEQ ID NO: 13) | pMaWo78 |
|  | MaWo206 | ggcgaagagtgttgcggcgggTTGGaTgttggcgggccatccgagcc (SEQ ID NO: 14) |  |

Example 4

Expression of the *Aspergillus fumigatus* cDNA Encoding Family GH6A Cellobiohydrolase II Variants in *Aspergillus oryzae* JaL355

*Aspergillus oryzae* JaL355 protoplasts were prepared according to the method of Christensen et al., 1988, *Bio/Technology* 6: 1419-1422. Five μg of expression vector (pMaWo55, pMaWo58, pAhyG90, pMaWo70, pMaWo71, pMaWo72, pMaWo73, pAhyG108, pAhyG111, or pMaWo78) was used to transform *A. oryzae* JaL355. Expression vector pAILo33 was transformed into *A. oryzae* JaL355 for expression of the *Aspergillus fumigatus* Family GH6A cellobiohydrolase II gene.

The transformation of *A. oryzae* JaL355 with pAILo33, pMaWo55, pMaWo58, pAhyG90, pMaWo70, pMaWo71, pMaWo72, pMaWo73, pAhyG108, pAhyG111, or pMaWo78 yielded about 1-10 transformants for each vector. Up to four transformants for each transformation were isolated to individual PDA plates.

Confluent PDA plates of the transformants were washed with 8 ml of 0.01% TWEEN® 20 and inoculated separately into 1 ml of MDU2BP medium in sterile 24 well tissue culture plates and incubated at 34° C. Three days after incubation, 20 μl of harvested broth from each culture was analyzed using 8-16% Tris-Glycine SDS-PAGE gels (Invitrogen, Carlsbad, Calif., USA) according to the manufacturer's instructions. SDS-PAGE profiles of the cultures showed that several transformants had a new major band of approximately 75 kDa.

A confluent plate of one transformant for each transformation (grown on PDA) was washed with 8 ml of 0.01% TWEEN® 20 and inoculated into 125 ml plastic shake flasks containing 25 ml of MDU2BP medium and incubated at 34° C., either stationary or at 200 rpm to generate broth for characterization of the enzyme. The flasks were harvested on day 3 and filtered using a 0.22 μm GP Express plus Membrane (Millipore, Bedford, Mass., USA).

Example 5

Measuring Thermostability of *Aspergillus fumigatus* Family GH6A Cellobiohydrolase II Variants Three ml of filtered broth for tested cultures from Example 4 were desalted into 100 mM NaCl-50 mM sodium acetate pH 5.0 using ECONO-PAC® 10DG Desalting Columns (Bio-Rad Laboratories, Inc., Hercules, Calif., USA). Protein in the desalted broths was concentrated to a 0.5 ml volume using a VIVASPIN® 6 (5 kDa cutoff) ultrafilter (Argos Technology, Elgin, Ill., USA).

The concentrated broths were diluted to 1 mg/ml protein concentration using 100 mM NaCl-50 mM sodium acetate pH 5.0. Two 25 μl aliquots of each 1 mg/ml protein sample were added to THERMOWELL® tube strip PCR tubes (Corning, Corning, N.Y., USA). One aliquot was kept on ice while the other aliquot was heated in an EPPENDORF® MASTERCYCLER® ep gradient S thermocycler (Eppendorf Scientific, Inc., Westbury, N.Y., USA) for 20 minutes at 68° C. and then cooled to 4° C. before being placed on ice. Both samples were then diluted with 175 μl of 0.0114% TWEEN® 20-100 mM NaCl-50 mM sodium acetate pH 5.0.

Residual activity of the heated samples was then measured by determining the activity of the heated samples and the samples kept on ice in hydrolysis of phosphoric acid swollen cellulose (PASC). Ten microliters of each sample was added in triplicate to a 96 well PCR plate (Eppendorf, Westbury, N.Y., USA). Then 190 μl of 2.1 g/l PASC in 0.01% TWEEN® 20-50 mM sodium acetate pH 5.0 buffer was added to the 10 μl of sample and mixed. Glucose standards at 100, 75, 50, 25, 12.5 and 0 mg per liter in 50 mM sodium acetate pH 5.0 buffer were added in duplicate at 200 μl per well. The resulting mixtures were incubated for 30 minutes at 50° C. in an EPPENDORF® MASTERCYCLER® ep gradient S thermocycler. The reactions were stopped by addition of 50 μl of 0.5 M NaOH to each well, including the glucose standards. The plate was then centrifuged in a SORVALL® RT 6000D centrifuge (Thermo Scientific, Waltham, Mass., USA) with a SORVALL® 1000B rotor equipped with a microplate carrier (Thermo Scientific, Waltham, Mass., USA) for 2 minutes at 2,000 rpm.

Activity on PASC was determined by measuring reducing ends released during a 30 minute hydrolysis at 50° C. One hundred microliters of each supernatant from the centrifuged plate was transferred to a separate 96-well PCR plate. Fifty microliters of 1.5% (w/v) PHBAH (4-hydroxy-benzhydride, Sigma Chemical Co., St. Louis, Mo., USA) in 0.5 M NaOH were added to each well. The plate was then heated in an EPPENDORF® MASTERCYCLER® ep gradient S thermocycler at 95° C. for 15 minutes and then 15° C. for 5 minutes. A total of 100 μl of each sample was transferred to a clear, flat-bottom 96-well plate (Corning, Inc., Corning, N.Y., USA). The absorbance at 410 nm was then measured using a SPECTRAMAX® 340 pc spectrophotometric plate reader (Molecular Devices, Sunnyvale, Calif., USA). The concentration of reducing ends released was determined from a straight-line fit to the concentration of reducing ends released versus the absorbance at 410 nm for the glucose standards. Residual activity was then calculated by dividing the reducing ends released from PASC hydrolyzed by a heated sample by the reducing ends released from PASC hydrolyzed by a sample that was kept on ice. Activity of the cellobiohydrolase II variants was compared to activity of the parent enzyme.

Figure 1B:
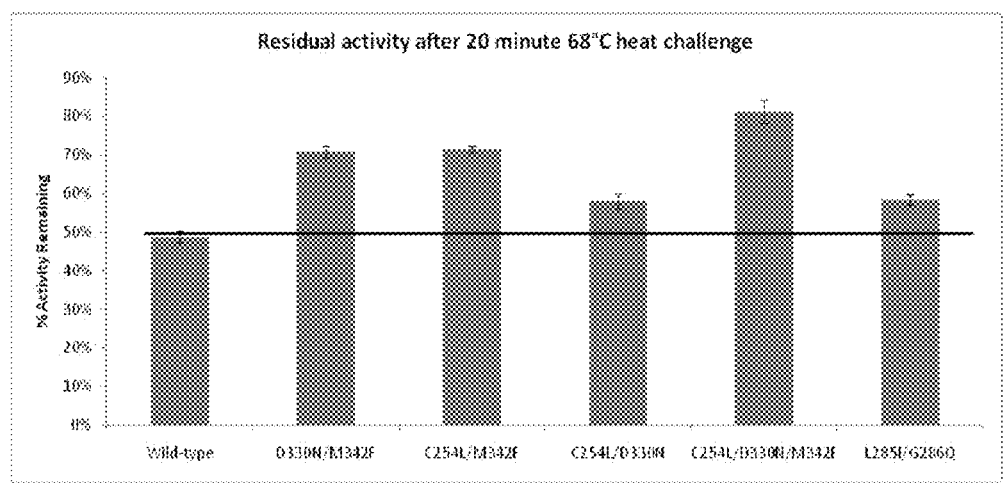
FIG. 1B shows a comparison of the residual activity for wild-type *Aspergillus fumigatus* family GH6A cellobiohydrolase and several combined variants of the *Aspergillus fumigatus* family GH6A cellobiohydrolase.

The results shown in FIGS. 1A and 1B demonstrated an increase in thermostability by a higher residual activity for indicated variants compared to the parent enzyme.

Example 6

Measuring Hydrolytic Activity of *Aspergillus fumigatus* Family GH6A Cellobiohydrolase II Variants One hundred fifty ml of broth supernatant containing *Aspergillus fumigatus* Family GH6A cellobiohydrolase II wild-type or variants pAhyG108, pAhyG111 or pMaWo73, were concentrated using a 10 kDa cut-off Vivaspin ultra-filter (Millipore, Billerica, Mass., USA). Up to 13 ml of concentrated samples were loaded on a HiLoad® 26/60 Superdex 200 column (GE Healthcare Life Sciences, Piscataway, N.J., USA) equilibrated with 100 mM NaCl-20 mM sodium acetate pH 5.0 buffer. Protein was eluted with 100 mM sodium chloride-20 mM sodium acetate pH 5.0 buffer. Fractions of 7 ml were collected for each sample and submitted to SDS-PAGE analysis on a 8-16% Bior-Rad Criterion stain-free Tris-HCl gel (Bio-Rad Laboratories, Inc., Hercules, Calif., USA). Fractions that eluted at 230 to 240 ml were pooled and showed greater than 95% purity.

The purified samples were diluted to 125, 112.5, 101.3, 91.1, 82.0, 73.8 and 66.4 µg/ml protein concentrations using 50 mM sodium acetate pH 5.0. Hydrolytic activity of the samples was then measured by hydrolyzing phosphoric acid swollen cellulose (PASC). Ten microliters of each sample was added in triplicate to a 96 well PCR plate (Eppendorf, Westbury, N.Y., USA). Then 190 µl of 2.1 g/l PASC in 0.01% TWEEN® 20-50 mM sodium acetate pH 5.0 buffer was added to the 10 µl of sample and mixed. Glucose standards at 100, 75, 50, 25, 12.5 and 0 mg per liter in 50 mM sodium acetate pH 5.0 buffer were added in duplicate at 200 µl per well. The resulting mixtures were incubated for 30 minutes at 50° C. in an EPPENDORF®MASTERCYCLER® ep gradient S thermocycler. The reactions were stopped by addition of 50 µl of 0.5 M NaOH to each well, including the glucose standards. The plate was then centrifuged in a SORVALL® RT 6000D centrifuge (Thermo Scientific, Waltham, Mass., USA) with a SORVALL® 1000B rotor equipped with a microplate carrier (Thermo Scientific, Waltham, Mass., USA) for 2 minutes at 2,000 rpm.

Activity on PASC was determined by measuring reducing ends released during a 30 minute hydrolysis at 50° C. One hundred microliters of each supernatant from the centrifuged plate was transferred to a separate 96-well PCR plate. Fifty microliters of 1.5% (w/v) PHBAH (4-hydroxy-benzhydride, Sigma Chemical Co., St. Louis, Mo., USA) in 0.5 M NaOH were added to each well. The plate was then heated in an EPPENDORF® MASTERCYCLER® ep gradient S thermocycler at 95° C. for 15 minutes and then 15° C. for 5 minutes. A total of 100 µl of each sample was transferred to a clear, flat-bottom 96-well plate (Corning, Inc., Corning, N.Y., USA). The absorbance at 410 nm was then measured using a SPECTRAMAX® 340 pc spectrophotometric plate reader (Molecular Devices, Sunnyvale, Calif., USA). The concentration of reducing ends released was determined from a straight-line fit to the concentration of reducing ends released versus the absorbance at 410 nm for the glucose standards. Activity of the cellobiohydrolase II variants was compared to activity of the parent enzyme.

Figure 2:
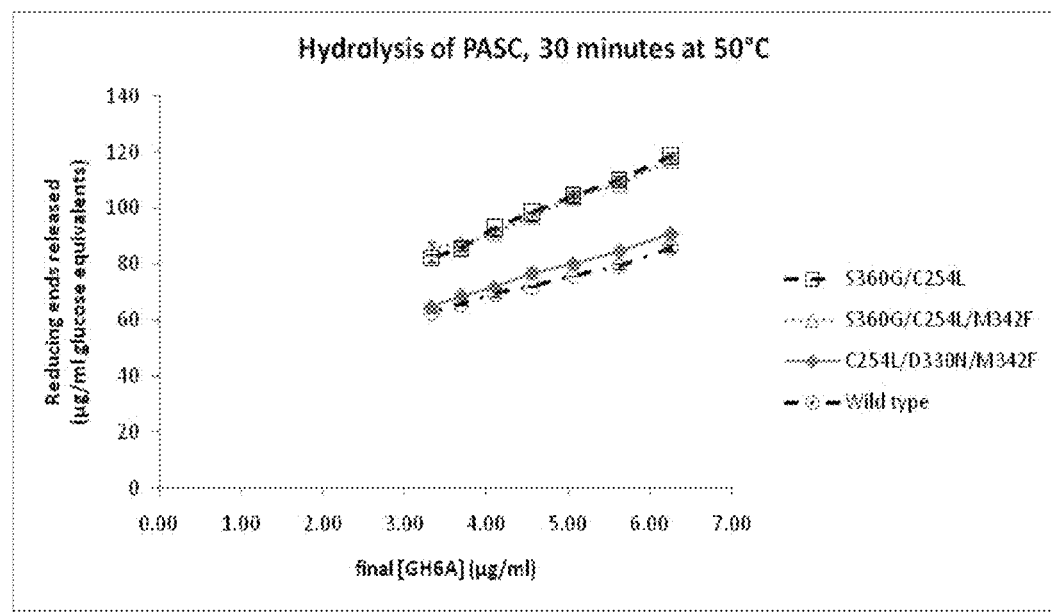
FIG. 2 shows a comparison of the hydrolytic activity for wild-type *Aspergillus fumigatus* family GH6A cellobiohydrolase and several combined variants of the *Aspergillus fumigatus* family GH6A cellobiohydrolase.

The results shown in FIG. 2 demonstrated an increase in hydrolytic activity of each variant containing the S360G mutation compared to the parent enzyme.

The present invention may be further described by the following numbered paragraphs:

[1] An isolated variant of a parent cellobiohydrolase, comprising a substitution at one or more (several) positions corresponding to positions 254, 285, 286, 330, 342, and 360 of SEQ ID NO: 2, wherein the variant has cellobiohydrolase activity.

[2] The variant of paragraph 1, wherein the parent cellobiohydrolase is:
 a. a polypeptide having at least 60% sequence identity to the mature polypeptide of SEQ ID NO: 2;
 b. a polypeptide encoded by a polynucleotide that hybridizes under low stringency conditions with (i) the mature polypeptide genomic coding sequence of SEQ ID NO: 1, (ii) the mature polypeptide cDNA coding sequence contained in SEQ ID NO: 1, or (iii) the full-length complementary strand of (i) or (ii);
 c. a polypeptide encoded by a polynucleotide having at least 60% identity to the mature polypeptide genomic coding sequence of SEQ ID NO: 1, or the mature polypeptide cDNA coding sequence contained in SEQ ID NO: 1;
 d. a fragment of the mature polypeptide of SEQ ID NO: 2, which has cellobiohydrolase activity.

[3] The variant of paragraph 1 or 2, wherein the parent cellobiohydrolase has at least 60%, e.g., at least 65%, at least 70%, at least 75%, at least 80%, at least 85%, at least 90%, at least 95%, at least 96%, at least 97%, at least 98%, at least 99% or 100% sequence identity to the mature polypeptide of SEQ ID NO: 2.

[4] The variant of any one of paragraphs 1-3, wherein the parent cellobiohydrolase is encoded by a polynucleotide that hybridizes under low stringency conditions with (i) the mature polypeptide genomic coding sequence of SEQ ID NO: 1, (ii) the mature polypeptide cDNA coding sequence contained in SEQ ID NO: 1, or (iii) the full-length complementary strand of (i) or (ii).

[5] The variant of any one of paragraphs 1-4, wherein the parent cellobiohydrolase is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to the mature polypeptide genomic coding sequence of SEQ ID NO: 1, or the mature polypeptide cDNA coding sequence contained in SEQ ID NO: 1.

[6] The variant of any one of paragraphs 1-5, wherein the parent cellobiohydrolase comprises or consists of the mature polypeptide of SEQ ID NO: 2.

[7] The variant of any one of paragraphs 1-5, wherein the parent cellobiohydrolase is a fragment of the mature polypeptide of SEQ ID NO: 2, wherein the fragment has cellobiohydrolase activity.

[8] The variant of any one of paragraphs 1-7, which has at least 60%, e.g., at least 65%, at least 70%, at least 75%, at least 80%, at least 85%, at least 90%, at least 95% identity, at least 96%, at least 97%, at least 98%, at least 99%, but less than 100%, sequence identity to the amino acid sequence of the parent cellobiohydrolase.

[9] The variant of any one of paragraphs 1-8, which has at least 60%, e.g., at least 65%, at least 70%, at least 75%, at least 80%, at least 85%, at least 90%, at least 95%, at least 96%, at least 97%, at least 98%, and at least 99%, but less than 100% sequence identity to the mature polypeptide of SEQ ID NO: 2.

[10] The variant of any one of paragraphs 1-9, wherein the variant comprises at least 370 amino acid residues, e.g., at least 390 or at least 410 amino acid residues.

[11] The variant of any one of paragraphs 1-10, wherein the variant comprises 1-5 substitutions, such as 1, 2, 3, 4, or 5 substitutions.

[12] The variant of any one of paragraphs 1-11, comprising a substitution at a position corresponding to position 254 of SEQ ID NO: 2.

[13] The variant of paragraph 12, wherein the substitution is with Leu.

[14] The variant of any one of paragraphs 1-13, comprising a substitution at a position corresponding to position 330 of SEQ ID NO: 2.

[15] The variant of paragraph 14, wherein the substitution is with Asn.

[16] The variant of any one of paragraphs 1-15, comprising a substitution at a position corresponding to position 342 of SEQ ID NO: 2.

[17] The variant of paragraph 16, wherein the substitution is with Phe.

[18] The variant of any one of paragraphs 1-17, comprising a substitution at a position corresponding to position 360 of SEQ ID NO: 2.

[19] The variant of paragraph 18, wherein the substitution is with Gly.

[20] The variant of any one of paragraphs 1-19, comprising a substitution at a position corresponding to position 285 of SEQ ID NO: 2.

[21] The variant of paragraph 20, wherein the substitution is with Ile.

[22] The variant of any one of paragraphs 1-21, comprising a substitution at a position corresponding to position 286 of SEQ ID NO: 2.

[23] The variant of paragraph 22, wherein the substitution is with Gln.

[24] The variant of any one of paragraphs 1-23, comprising substitutions at least two positions corresponding to any of positions 254, 285, 286, 330, 342, and 360 of SEQ ID NO: 2.

[25] The variant of any one of paragraphs 1-23, comprising substitutions at least three positions corresponding to any of positions 254, 285, 286, 330, 342, and 360 of SEQ ID NO: 2.

[26] The variant of any one of paragraphs 1-23, comprising substitutions at least four positions corresponding to any of positions 254, 285, 286, 330, 342, and 360 of SEQ ID NO: 2.

[27] The variant of any one of paragraphs 1-23, comprising substitutions at least five positions corresponding to any of positions 254, 285, 286, 330, 342, and 360 of SEQ ID NO: 2.

[27] The variant of any one of paragraphs 1-23, comprising substitutions at each position corresponding to any of positions 254, 285, 286, 330, 342, and 360 of SEQ ID NO: 2.

[28] The variant of any one of paragraphs 1-27, comprising one or more (several) substitutions selected from the group consisting of C254L, L285I, G286Q, D330N, M342F, and S360G.

[29] The variant of paragraph 28, comprising the substitution C254L.

[30] The variant of paragraph 28, comprising the substitution L285I.

[31] The variant of paragraph 28, comprising the substitution G286Q.

[32] The variant of paragraph 28, comprising the substitution D330N.

[33] The variant of paragraph 28, comprising the substitution M342F.

[34] The variant of paragraph 28, comprising the substitution S360G.

[35] The variant of paragraph 28, comprising two substitutions selected from the group consisting of C254L, L285I, G286Q, D330N, M342F, and S360G.

[36] The variant of paragraph 35, comprising the substitutions C254L+L285I.

[37] The variant of paragraph 35, comprising the substitutions C254L+G286Q.

[38] The variant of paragraph 35, comprising the substitutions C254L+D330N.

[39] The variant of paragraph 35, comprising the substitutions C254L+M342F.

[40] The variant of paragraph 35, comprising the substitutions C254L+S360G.

[41] The variant of paragraph 35, comprising the substitutions L285I+G286Q.

[42] The variant of paragraph 35, comprising the substitutions L285I+D330N.

[43] The variant of paragraph 35, comprising the substitutions L285I+M342F.

[44] The variant of paragraph 35, comprising the substitutions L285I+S360G.

[45] The variant of paragraph 35, comprising the substitutions G286Q+D330N.

[46] The variant of paragraph 35, comprising the substitutions G286Q+M342F.

[47] The variant of paragraph 35, comprising the substitutions G286Q+S360G.

[48] The variant of paragraph 28, comprising three substitutions selected from the group consisting of C254L, L285I, G286Q, D330N, M342F, and S360G.

[49] The variant of paragraph 48, comprising the substitutions C254L+L285I+G286Q.

[50] The variant of paragraph 48, comprising the substitutions C254L+L285I+D330N.

[51] The variant of paragraph 48, comprising the substitutions C254L+L285I+M342F.

[52] The variant of paragraph 48, comprising the substitutions C254L+L285I+S360G.

[53] The variant of paragraph 48, comprising the substitutions C254L+G286Q+D330N.

[54] The variant of paragraph 48, comprising the substitutions C254L+G286Q+M342F.

[55] The variant of paragraph 48, comprising the substitutions C254L+G286Q+S360G.

[56] The variant of paragraph 48, comprising the substitutions C254L+D330N+M342F.

[57] The variant of paragraph 48, comprising the substitutions C254L+D330N+S360G.

[58] The variant of paragraph 48, comprising the substitutions C254L+M342F+S360G.

[59] The variant of paragraph 48, comprising the substitutions L285I+G286Q+D330N.

[60] The variant of paragraph 48, comprising the substitutions L285I+G286Q+M342F.

[61] The variant of paragraph 48, comprising the substitutions L285I+G286Q+S360G.

[62] The variant of paragraph 48, comprising the substitutions L285I+D330N+M342F.

[63] The variant of paragraph 48, comprising the substitutions L285I+D330N+S360G.

[64] The variant of paragraph 48, comprising the substitutions L285I+M342F+S360G.

[65] The variant of paragraph 48, comprising the substitutions G286Q+D330N+M342F.

[66] The variant of paragraph 48, comprising the substitutions G286Q+D330N+S360G.

[67] The variant of paragraph 48, comprising the substitutions G286Q+M342F+S360G.

[68] The variant of paragraph 48, comprising the substitutions D330N+M342F+S360G.

[69] The variant of paragraph 28, comprising four substitutions selected from the group consisting of C254L, L285I, G286Q, D330N, M342F, and S360G.

[70] The variant of paragraph 69, comprising the substitutions C254L+L285I+G286Q+D330N.

[71] The variant of paragraph 69, comprising the substitutions C254L+L285I+G286Q+M342F.

[72] The variant of paragraph 69, comprising the substitutions C254L+L285I+D330N+M342F.

[73] The variant of paragraph 69, comprising the substitutions C254L+G286Q+D330N+M342F.

[74] The variant of paragraph 69, comprising the substitutions L285I+G286Q+D330N+M342F.

[75] The variant of paragraph 69, comprising the substitutions C254L+L285I+G286Q+S360G.

[76] The variant of paragraph 69, comprising the substitutions C254L+L285I+D330N+S360G.

[77] The variant of paragraph 69, comprising the substitutions C254L+G286Q+D330N+S360G.

[78] The variant of paragraph 69, comprising the substitutions L285I+G286Q+D330N+S360G.

[79] The variant of paragraph 69, comprising the substitutions C254L+L285I+M342F+S360G.

[80] The variant of paragraph 69, comprising the substitutions C254L+G286Q+M342F+S360G.

[81] The variant of paragraph 69, comprising the substitutions L285I+G286Q+M342F+S360G.

[82] The variant of paragraph 69, comprising the substitutions C254L+D330N+M342F+S360G.

[83] The variant of paragraph 69, comprising the substitutions L285I+D330N+M342F+S360G.

[84] The variant of paragraph 69, comprising the substitutions G286Q+D330N+M342F+S360G.

[85] The variant of paragraph 28, comprising five substitutions selected from the group consisting of C254L, L285I, G286Q, D330N, M342F, and S360G.

[86] The variant of paragraph 85, comprising the substitutions L285I+G286Q+D330N+M342F+S360G.

[87] The variant of paragraph 85, comprising the substitutions C254L+G286Q+D330N+M342F+S360G.

[88] The variant of paragraph 85, comprising the substitutions C254L+L285I+D330N+M342F+S360G.

[89] The variant of paragraph 85, comprising the substitutions C254L+L285I+G286Q+M342F+S360G.

[90] The variant of paragraph 85, comprising the substitutions C254L+L285I+G286Q+D330N+S360G.

[91] The variant of paragraph 85, comprising the substitutions C254L+L285I+G286Q+D330N+M342F.

[92] The variant of paragraph 28, comprising the substitutions C254L+L285I+G286Q+D330N+M342F+S360G.

[93] The variant of any one of paragraphs 1-92, further comprising one or more (several) substitutions at any position corresponding to positions 245, 382, 420, 437, and 440 of SEQ ID NO: 2.

[94] The variant of paragraph 93, comprising two substitutions at any position corresponding to positions 245, 382, 420, 437, and 440 of SEQ ID NO: 2.

[95] The variant of paragraph 93, comprising three substitutions at any position corresponding to positions 245, 382, 420, 437, and 440 of SEQ ID NO: 2.

[96] The variant of paragraph 93, comprising four substitutions at any position corresponding to positions 245, 382, 420, 437, and 440 of SEQ ID NO: 2.

[97] The variant of paragraph 93, comprising substitutions at each position corresponding to positions 245, 382, 420, 437, and 440 of SEQ ID NO: 2.

[98] The variant of any one of paragraphs 93-97, comprising a substitution at a position corresponding to position 245 of SEQ ID NO: 2.

[99] The variant of paragraph 98, wherein the substitution is Ser.

[100] The variant of any one of paragraphs 93-99, comprising a substitution at a position corresponding to position 382 of SEQ ID NO: 2.

[101] The variant of paragraph 100, wherein the substitution is Cys.

[102] The variant of any one of paragraphs 93-101, comprising a substitution at a position corresponding to position 420 of SEQ ID NO: 2.

[103] The variant of paragraph 102, wherein the substitution is Ile.

[104] The variant of any one of paragraphs 93-103, comprising a substitution at a position corresponding to position 437 of SEQ ID NO: 2.

[105] The variant of paragraph 104, wherein the substitution is Gln.

[106] The variant of any one of paragraphs 93-105, comprising a substitution at a position corresponding to position 440 of SEQ ID NO: 2.

[107] The variant of paragraph 106, wherein the substitution is Cys.

[108] The variant of any one of paragraphs 93-107, comprising one or more (several) substitutions selected from the group consisting of A245S, G382C, L420I, T437Q, and Q440C.

[109] The variant of paragraph 108, comprising two substitutions selected from the group consisting of A245S, G382C, L420I, T437Q, and Q440C.

[110] The variant of paragraph 109, comprising the substitutions L420I+T437Q.

[111] The variant of paragraph 109, comprising the substitutions A245S+L420I.

[112] The variant of paragraph 109, comprising the substitutions G382C+L420I.

[113] The variant of paragraph 109, comprising the substitutions L420I+Q440C.

[114] The variant of paragraph 109, comprising the substitutions A245S+T437Q.

[115] The variant of paragraph 109, comprising the substitutions G382C+T437Q.

[116] The variant of paragraph 109, comprising the substitutions T437Q+Q440C.

[117] The variant of paragraph 109, comprising the substitutions A245S+G382C.

[118] The variant of paragraph 109, comprising the substitutions A245S+Q440C.

[119] The variant of paragraph 109, comprising the substitutions G382C+Q440C.

[120] The variant of paragraph 108, comprising three substitutions selected from the group consisting of A245S, G382C, L420I, T437Q, and Q440C.

[121] The variant of paragraph 120, comprising the substitutions A245S+L420I+T437Q.

[122] The variant of paragraph 120, comprising the substitutions G382C+L420I+T437Q.

[123] The variant of paragraph 120, comprising the substitutions L420I+T437Q+Q440C.

[124] The variant of paragraph 120, comprising the substitutions A245S+G382C+L420I.

[125] The variant of paragraph 120, comprising the substitutions A245S+L420I+Q440C.

[126] The variant of paragraph 120, comprising the substitutions G382C+L420I+Q440C.

[127] The variant of paragraph 120, comprising the substitutions A245S+G382C+T437Q.

[128] The variant of paragraph 120, comprising the substitutions A245S+T437Q+Q440C.

[129] The variant of paragraph 120, comprising the substitutions G382C+T437Q+Q440C.

[130] The variant of paragraph 120, comprising the substitutions A245S+G382C+Q440C.

[131] The variant of paragraph 108, comprising four substitutions selected from the group consisting of A245S, G382C, L420I, T437Q, and Q440C.

[132] The variant of paragraph 131, comprising the substitutions A245S+G382C+T437Q+Q440C.

[133] The variant of paragraph 131, comprising the substitutions A245S+G382C+L420I+Q440C.

[134] The variant of paragraph 131, comprising the substitutions G382C+L420I+T437Q+Q440C.

[135] The variant of paragraph 131, comprising the substitutions A245S+L420I+T437Q+Q440C.

[136] The variant of paragraph 131, comprising the substitutions A245S+G382C+L420I+T437Q.

[137] The variant of paragraph 108, comprising the substitutions A245S+G382C+L420I+T437Q+Q440C.

[138] The variant of any one of paragraphs 1-137, which has improved thermostability relative to the parent cellobiohydrolase.

[139] The variant of any one of paragraphs 1-138, wherein the mature polypeptide is amino acids 20-454 of SEQ ID NO:2.

[140] The variant of any one of paragraphs 1-139, wherein the mature polypeptide coding sequence is nucleotides 58-1710 of SEQ ID NO: 1.

[141] An isolated polynucleotide encoding the variant of any one of paragraphs 1-140.

[142] A nucleic acid construct comprising the polynucleotide of paragraph 141.

[143] An expression vector comprising the polynucleotide of paragraph 141.

[144] A host cell comprising the polynucleotide of paragraph 141.

[145] A method of producing a variant of a parent cellobiohydrolase, comprising:
(a) cultivating the host cell of paragraph 144 under conditions suitable for the expression of the variant; and
(b) recovering the variant.

[146] A transgenic plant, plant part or plant cell transformed with the polynucleotide of paragraph 141.

[147] A method of producing a variant of any one of paragraphs 1-140, comprising:
(a) cultivating a transgenic plant or a plant cell comprising a polynucleotide encoding the variant under conditions conducive for production of the variant; and
(b) recovering the variant.

[148] A method for obtaining the variant of any one of paragraphs 1-140, comprising:
(a) introducing into a parent cellobiohydrolase a substitution at one or more (several) positions corresponding to positions 254, 285, 286, 330, 342, and 360 of the mature polypeptide of SEQ ID NO: 2, wherein the variant has cellobiohydrolase activity; and
(b) recovering the variant.

[149] The method of paragraph 148 further comprising introducing into the parent cellobiohydrolase a substitution at one or more (several) positions corresponding to positions 245, 382, 420, 437, and 440 of the mature polypeptide of SEQ ID NO: 2

[150] An enzyme composition comprising the variant of any one of paragraphs 1-140.

[151] The enzyme composition of paragraph 150, further comprising a cellulolytic enzyme selected from the group consisting of an endoglucanase, a cellobiohydrolase, and a beta-glucosidase.

[152] The enzyme composition of paragraph 150 or 151, further comprising a polypeptide having cellulolytic enhancing activity.

[153] The enzyme composition of any one of paragraphs 150-152, further comprising an enzyme selected from the group consisting of a xylanase, a hemicellulase, an esterase, a protease, a laccase, and a peroxidase.

[154] A method for degrading or converting a cellulosic material, comprising: treating the cellulosic material with an enzyme composition of any one of paragraphs 150-153.

[155] The method of paragraph 154, wherein the cellulosic material is pretreated.

[156] The method of paragraph 154 or 155, further comprising recovering the degraded cellulosic material.

[157] The method of paragraph 156, wherein the degraded cellulosic material is a sugar.

[158] The method of paragraph 157, wherein the sugar is selected from the group consisting of glucose, xylose, mannose, galactose, and arabinose.

[159] A method for producing a fermentation product from cellulosic material, comprising:
(a) saccharifying the cellulosic material with an enzyme composition of any of claims 150-153 to produce saccharified cellulosic material;
(b) fermenting the saccharified cellulosic material with one or more fermenting microorganisms to produce a fermentation product; and
(c) recovering the fermentation product.

[160] The method of paragraph 159, wherein the cellulosic material is pretreated.

[161] The method of paragraph 159 or 160, wherein steps (a) and (b) are performed simultaneously.

[162] The method of any one of paragraphs 159-161, wherein the fermentation product is an alcohol, an organic acid, a ketone, an amino acid, or a gas.

[163] A method of fermenting a cellulosic material, comprising: fermenting the cellulosic material with one or more fermenting microorganisms, wherein the cellulosic material is saccharified with an enzyme composition of any one of paragraphs 150-153.

[164] The method of paragraph 163, wherein the fermenting of the cellulosic material produces a fermentation product.

[165] The method of paragraph 163 or 164, further comprising recovering the fermentation product.

[166] The method of any one of paragraphs 163-165, wherein the cellulosic material is pretreated before being saccharified.

[167] The method of any one of paragraphs 163-166, wherein the fermentation product is an alcohol, an organic acid, a ketone, an amino acid, or a gas.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims.In the case of conflict, the present disclosure including definitions will control.

What is claimed is:

1. An isolated variant of a parent cellobiohydrolase, comprising a substitution at one or more positions corresponding to positions 254, 285, 286, 330, 342, and 360 of SEQ ID NO: 2, wherein the variant has cellobiohydrolase activity and wherein the parent cellobiohydrolase is selected from the group consisting of:
   (a) a polypeptide having at least 90% sequence identity to the mature polypeptide of SEQ ID NO: 2;
   (b) a polypeptide encoded by a polynucleotide that hybridizes under very high stringency conditions with (i) the mature polypeptide genomic coding sequence of SEQ ID NO: 1, (ii) the mature polypeptide cDNA coding sequence contained in SEQ ID NO: 1, or (iii) the full-length complementary strand of (i) or (ii), wherein very high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 70° C.;
   (c) a polypeptide encoded by a polynucleotide having at least 90% sequence identity to the mature polypeptide genomic coding sequence of SEQ ID NO: 1, or the mature polypeptide cDNA coding sequence contained in SEQ ID NO: 1; and
   (d) a fragment of the mature polypeptide of SEQ ID NO: 2, which has cellobiohydrolase activity.

2. The variant of claim 1, wherein the parent cellobiohydrolase comprises or consists of the mature polypeptide of SEQ ID NO: 2.

3. The variant of claim 1, wherein the substitution corresponding to position 254 is with Leu, the substitution corresponding to position 285 is with Ile, the substitution corresponding to position 286 is with Gln, the substitution corresponding to position 330 is with Asn, the substitution corresponding to position 342 is with Phe, and the substitution corresponding to position 360 is with Gly.

4. The variant of claim 1, wherein the substitution corresponding to position 254 is C254L, the substitution corresponding to position 285 is L285I, the substitution corresponding to position 286 is G286Q, the substitution corresponding to position 330 is D330N, the substitution corresponding to position 342 is M342F, and the substitution corresponding to position 360 is S360G.

5. The variant of claim 1, further comprising a substitution at one or more positions corresponding to positions 245, 382, 420, 437, and 440 of SEQ ID NO: 2.

6. The variant of claim 5, wherein the substitution corresponding to position 245 is with Ser, the substitution corresponding to position 382 is with Cys, the substitution corresponding to position 420 is with Ile, the substitution corresponding to position 437 is with Gln, and the substitution corresponding to position 440 is with Cys.

7. The variant of claim 5, wherein the substitution corresponding to position corresponding to position 245 is A245S, the substitution corresponding to position 382 is G382C, the substitution corresponding to position 420 is L420I, the substitution corresponding to position 437 is T437Q, and the substitution corresponding to position 440 is Q440C.

8. The variant of claim 1, which has improved thermostability relative to the parent cellobiohydrolase.

9. The variant of claim 1, wherein the mature polypeptide of SEQ ID NO: 2 is amino acids 20-454 of SEQ ID NO: 2.

10. The variant of claim 1, wherein the mature polypeptide coding sequence of SEQ ID NO: 1 is nucleotides 58-1710 of SEQ ID NO: 1.

11. An isolated polynucleotide encoding the variant of claim 1.

12. A nucleic acid construct comprising the polynucleotide of claim 11.

13. An expression vector comprising the polynucleotide of claim 11.

14. An isolated host cell comprising the polynucleotide of claim 11.

15. A method of producing a variant of a parent cellobiohydrolase, comprising: (a) cultivating the host cell of claim 14 under conditions suitable for the expression of the variant; and (b) recovering the variant.

16. A method for obtaining the variant of claim 1, comprising: (a) introducing into a parent cellobiohydrolase a substitution at one or more positions corresponding to positions 254, 285, 286, 330, 342, and 360 of SEQ ID NO: 2; and (b) recovering the variant.

17. An enzyme composition comprising the variant of claim 1.

18. The enzyme composition of claim 17, further comprising a cellulolytic enzyme selected from the group consisting of an endoglucanase, a cellobiohydrolase, and a beta-glucosidase, and optionally further comprises a polypeptide having cellulolytic enhancing activity, a xylanase, a hemicellulase, an esterase, a protease, a laccase, or a peroxidase.

19. A method for degrading or converting a cellulosic material, comprising: treating the cellulosic material with an enzyme composition of claim 17.

20. A method for producing a fermentation product from cellulosic material, comprising:
  (a) saccharifying the cellulosic material with an enzyme composition of claim 17 to produce saccharified cellulosic material;
  (b) fermenting the saccharified cellulosic material with one or more fermenting microorganisms to produce a fermentation product; and
  (c) recovering the fermentation product.

21. A method of fermenting a cellulosic material, comprising:
  fermenting the cellulosic material with one or more fermenting microorganisms, wherein the cellulosic material is saccharified with an enzyme composition of claim 17.

22. The variant of claim 1, wherein the parent cellobiohydrolase is a polypeptide having at least 91%, at least 92%, at least 93%, at least 94%, at least 95%, at least 96%, at least 97%, at least 98%, or at least 99% sequence identity to the mature polypeptide of SEQ ID NO: 2.

23. The variant of claim 1, wherein the parent cellobiohydrolase is encoded by a polynucleotide having at least 91%, at least 92%, at least 93%, at least 94%, at least 95%, at least 96%, at least 97%, at least 98%, or at least 99% sequence identity to the mature polypeptide genomic coding sequence of SEQ ID NO: 1, or the mature polypeptide cDNA coding sequence contained in SEQ ID NO: 1.

* * * * *

SEQUENCE LISTING

<160> NUMBER OF SEQ ID NOS: 14

<210> SEQ ID NO 1
<211> LENGTH: 1713
<212> TYPE: DNA
<213> ORGANISM: Aspergillus fumigatus

<400> SEQUENCE: 1

| | | | | | |
|---|---|---|---|---|---|
| atgaagcacc | ttgcatcttc | catcgcattg | actctactgt | tgcctgccgt | gcaggcccag | 60 |
| cagaccgtat | ggggccaatg | tatgttctgg | ctgtcactgg | aataagactg | tatcaactgc | 120 |
| tgatatgctt | ctaggtggcg | gccaaggctg | gtctggcccg | acgagctgtg | ttgccggcgc | 180 |
| agcctgtagc | acactgaatc | cctgtatgtt | agatatcgtc | ctgagtggag | acttatactg | 240 |
| acttccttag | actacgctca | gtgtatcccg | ggagccaccg | cgacgtccac | taccctcacg | 300 |
| acgacgacgg | cggcgacgac | gacatcccag | accaccacca | aacctaccac | gactggtcca | 360 |
| actacatccg | cacccaccgt | gaccgcatcc | ggtaacccct | tcagcggcta | ccagctgtat | 420 |
| gccaacccct | actactcctc | cgaggtccat | actctggcca | tgccttctct | gcccagctcg | 480 |
| ctgcagccca | aggctagtgc | tgttgctgaa | gtgccctcat | ttgtttggct | gtaagtggcc | 540 |
| ttatcccaat | actgagacca | actctctgac | agtcgtagcg | acgttgccgc | caaggtgccc | 600 |
| actatgggaa | cctacctggc | cgacattcag | gccaagaaca | aggccggcgc | caaccctcct | 660 |
| atcgctggta | tcttcgtggt | ctacgacttg | ccggaccgtg | actgcgccgc | tctggccagt | 720 |
| aatggcgagt | actcaattgc | caacaacggt | gtggccaact | acaaggcgta | cattgacgcc | 780 |
| atccgtgctc | agctggtgaa | gtactctgac | gttcacacca | tcctcgtcat | cggtaggccg | 840 |
| tacacctccg | ttgcgcgccg | cttttctctg | acatcttgca | gaacccgaca | gcttggccaa | 900 |
| cctggtgacc | aacctcaacg | tcgccaaatg | cgccaatgcg | cagagcgcct | acctggagtg | 960 |
| tgtcgactat | gctctgaagc | agctcaacct | gcccaacgtc | gccatgtacc | tcgacgcagg | 1020 |
| tatgcctcac | ttcccgcatt | ctgtatccct | tccagacact | aactcatcag | gccatgcggg | 1080 |
| ctggctcgga | tggcccgcca | acttgggccc | gccgcaaca | ctcttcgcca | aagtctacac | 1140 |
| cgacgcgggt | tccccgcgg | ctgttcgtgg | cctggccacc | aacgtcgcca | actacaacgc | 1200 |
| ctggtcgctc | agtacctgcc | cctcctacac | ccagggagac | cccaactgcg | acgagaagaa | 1260 |
| gtacatcaac | gccatggcgc | ctcttctcaa | ggaagccggc | ttcgatgccc | acttcatcat | 1320 |
| ggatacctgt | aagtgcttat | tccaatcgcc | gatgtgtgcc | gactaatcaa | tgtttcagcc | 1380 |
| cggaatggcg | tccagcccac | gaagcaaaac | gcctggggtg | actggtgcaa | cgtcatcggc | 1440 |
| accggcttcg | gtgttcgccc | ctcgactaac | accggcgatc | cgctccagga | tgcctttgtg | 1500 |
| tggatcaagc | ccggtggaga | gagtgatggc | acgtccaact | cgacttcccc | ccggtatgac | 1560 |
| gcgcactgcg | gatatagtga | tgctctgcag | cctgctcctg | aggctggtac | ttggttccag | 1620 |
| gtatgtcatc | cattagccag | atgagggata | agtgactgac | ggacctaggc | ctactttgag | 1680 |
| cagcttctga | ccaacgctaa | cccgtccttt | taa | | | 1713 |

<210> SEQ ID NO 2
<211> LENGTH: 454
<212> TYPE: PRT
<213> ORGANISM: Aspergillus fumigatus

<400> SEQUENCE: 2

Met Lys His Leu Ala Ser Ser Ile Ala Leu Thr Leu Leu Leu Pro Ala
1               5                   10                  15

```
Val Gln Ala Gln Gln Thr Val Trp Gly Gln Cys Gly Gly Gln Gly Trp
                20                  25                  30

Ser Gly Pro Thr Ser Cys Val Ala Gly Ala Ala Cys Ser Thr Leu Asn
            35                  40                  45

Pro Tyr Tyr Ala Gln Cys Ile Pro Gly Ala Thr Ala Thr Ser Thr Thr
        50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
        195                 200                 205

Asp Ala Ile Arg Ala Gln Leu Val Lys Tyr Ser Asp Val His Thr Ile
    210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
        275                 280                 285

Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

Lys Tyr Ile Asn Ala Met Ala Pro Leu Leu Lys Glu Ala Gly Phe Asp
            340                 345                 350

Ala His Phe Ile Met Asp Thr Ser Arg Asn Gly Val Gln Pro Thr Lys
        355                 360                 365

Gln Asn Ala Trp Gly Asp Trp Cys Asn Val Ile Gly Thr Gly Phe Gly
    370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
            420                 425                 430

Pro Glu Ala Gly Thr Trp Phe Gln Ala Tyr Phe Glu Gln Leu Leu Thr
```

```
            435                 440                 445
Asn Ala Asn Pro Ser Phe
    450

<210> SEQ ID NO 3
<211> LENGTH: 37
<212> TYPE: DNA
<213> ORGANISM: Aspergillus fumigatus

<400> SEQUENCE: 3
actggattta ccatgaagca ccttgcatct tccatcg                              37

<210> SEQ ID NO 4
<211> LENGTH: 34
<212> TYPE: DNA
<213> ORGANISM: Aspergillus fumigatus

<400> SEQUENCE: 4
tcacctctag ttaattaaaa ggacgggtta gcgt                                 34

<210> SEQ ID NO 5
<211> LENGTH: 30
<212> TYPE: DNA
<213> ORGANISM: Aspergillus fumigatus

<400> SEQUENCE: 5
cctacaccca gggaaacccc aactgcgacg                                      30

<210> SEQ ID NO 6
<211> LENGTH: 30
<212> TYPE: DNA
<213> ORGANISM: Aspergillus fumigatus

<400> SEQUENCE: 6
cgtcgcagtt ggggtttccc tgggtgtagg                                      30

<210> SEQ ID NO 7
<211> LENGTH: 38
<212> TYPE: DNA
<213> ORGANISM: Aspergillus fumigatus

<400> SEQUENCE: 7
gagcgcctac ctggagcttg tcgactatgc tctgaagc                             38

<210> SEQ ID NO 8
<211> LENGTH: 38
<212> TYPE: DNA
<213> ORGANISM: Aspergillus fumigatus

<400> SEQUENCE: 8
gcttcagagc atagtcgaca agctccaggt aggcgctc                             38

<210> SEQ ID NO 9
<211> LENGTH: 44
<212> TYPE: DNA
<213> ORGANISM: Aspergillus fumigatus

<400> SEQUENCE: 9
gaagaagtac atcaacgcct ttgcgcctct tctcaaggaa gccg                      44

<210> SEQ ID NO 10
<211> LENGTH: 44
<212> TYPE: DNA
```

```
<213> ORGANISM: Aspergillus fumigatus

<400> SEQUENCE: 10
cggcttcctt gagaagaggc gcaaaggcgt tgatgtactt cttc                44

<210> SEQ ID NO 11
<211> LENGTH: 42
<212> TYPE: DNA
<213> ORGANISM: Aspergillus fumigatus

<400> SEQUENCE: 11
gcccacttca tcatggatac cgggcggaat ggcgtccagc cc                  42

<210> SEQ ID NO 12
<211> LENGTH: 42
<212> TYPE: DNA
<213> ORGANISM: Aspergillus fumigatus

<400> SEQUENCE: 12
gggctggacg ccattccgcc cggtatccat gatgaagtgg gc                  42

<210> SEQ ID NO 13
<211> LENGTH: 47
<212> TYPE: DNA
<213> ORGANISM: Aspergillus fumigatus

<400> SEQUENCE: 13
ggctcggatg gcccgccaac atccaacccg ccgcaacact cttcgcc             47

<210> SEQ ID NO 14
<211> LENGTH: 47
<212> TYPE: DNA
<213> ORGANISM: Aspergillus fumigatus

<400> SEQUENCE: 14
ggcgaagagt gttgcggcgg gttggatgtt ggcgggccat ccgagcc             47
```